(12) United States Patent
Wheeler et al.

(10) Patent No.: US 9,770,185 B2
(45) Date of Patent: Sep. 26, 2017

(54) SHARING A SINGLE ELECTRODE BETWEEN SKIN RESISTANCE AND CAPACITANCE MEASUREMENTS

(71) Applicant: Verily Life Sciences LLC, Mountain View, CA (US)

(72) Inventors: Patrick Lin Wheeler, San Jose, CA (US); Russell Norman Mirov, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 321 days.

(21) Appl. No.: 14/453,443

(22) Filed: Aug. 6, 2014

(65) Prior Publication Data
US 2016/0038055 A1    Feb. 11, 2016

(51) Int. Cl.
*A61B 5/053* (2006.01)
*A61B 5/00* (2006.01)
*A61B 5/01* (2006.01)

(52) U.S. Cl.
CPC ............ *A61B 5/0533* (2013.01); *A61B 5/681* (2013.01); *A61B 5/01* (2013.01); *A61B 2562/0214* (2013.01); *A61B 2562/18* (2013.01)

(58) Field of Classification Search
CPC ... A61B 5/053–5/0533; A61B 5/6802–5/6839; A61B 2562/0214
(Continued)

(56) References Cited

U.S. PATENT DOCUMENTS 3,207,151 A  *  9/1965  Takagi .................. A61B 5/0532
                                                                    128/907
3,648,686 A  *  3/1972  Payne .................. A61B 5/0533
                                                                    600/547
(Continued)

FOREIGN PATENT DOCUMENTS

WO     2006021820 A1     3/2006
WO     2013011416 A1     1/2013
WO     2013075270 A1     5/2013

OTHER PUBLICATIONS

Dozio, et al. "Time based measurement of the impedance of the skin-electrode interface for dry electrode ECG recording." Engineering in Medicine and Biology Society, 2007. EMBS 2007. 29th Annual International Conference of the IEEE. IEEE, 2007.*
(Continued)

*Primary Examiner* — David J McCrosky
(74) *Attorney, Agent, or Firm* — McDonnell Boehnen Hulbert & Berghoff LLP

(57) ABSTRACT

Wearable devices are described herein including a housing and a mount configured to mount the housing to an external surface of a wearer. The wearable devices further include first and second electrical contacts protruding from the housing and configured such that the electrical contacts can be used to measure a Galvanic skin resistance of skin proximate to the electrical contacts when the wearable device is mounted to the external surface of the wearer. The electrical contacts are additionally configured to measure a capacitance between electrical contacts. The measured capacitance between the electrical contacts could be related to a capacitance of skin proximate to the electrical contacts when the wearable device is mounted to the external surface of the wearer. The wearable devices further include an electronically switched capacitor connected between the electrical contacts that can be operated to enable the Gal-
(Continued)

vanic skin resistance and capacitance measurements described above.

20 Claims, 11 Drawing Sheets

(58) Field of Classification Search
USPC .................................................. 600/547, 306
See application file for complete search history.

(56) References Cited

U.S. PATENT DOCUMENTS

| | | | | |
|---|---|---|---|---|
| 3,866,600 A * | 2/1975 | Rey | ...................... | A61B 5/0531 600/547 |
| 3,870,034 A * | 3/1975 | James | .................. | A61B 5/0531 600/547 |
| 3,901,214 A * | 8/1975 | Taaffe | .................. | A61B 5/0531 600/547 |
| 4,365,637 A * | 12/1982 | Johnson | ............... | A61B 5/0531 600/547 |
| 4,509,531 A | 4/1985 | Ward | | |
| 5,385,150 A * | 1/1995 | Ishikawa | .............. | A61B 5/0532 600/548 |
| 7,286,871 B2 * | 10/2007 | Cohen | ................ | A61B 5/04004 600/544 |
| 8,480,578 B2 * | 7/2013 | Jang | .................... | A61B 5/0537 600/306 |
| 9,454,503 B1 * | 9/2016 | Sizikov | ............... | G06F 13/4081 |
| 2003/0195585 A1 | 10/2003 | Gruzdowich et al. | | |
| 2010/0030167 A1 * | 2/2010 | Thirstrup | ................ | A61F 5/445 604/318 |
| 2011/0295087 A1 * | 12/2011 | Shinoda | ............... | A61B 5/0531 600/306 |
| 2012/0238890 A1 | 9/2012 | Baker et al. | | |
| 2013/0023751 A1 * | 1/2013 | Lichtenstein | ........ | A61B 5/6838 600/547 |
| 2013/0053661 A1 | 2/2013 | Alberth et al. | | |
| 2013/0119255 A1 | 5/2013 | Dickinson et al. | | |
| 2013/0211204 A1 | 8/2013 | Caduff et al. | | |
| 2014/0107493 A1 * | 4/2014 | Yuen | ..................... | A61B 5/681 600/473 |
| 2014/0343392 A1 | 11/2014 | Yang | | |

OTHER PUBLICATIONS

Apogee, "Lie Detector Electronic Kit ML101", Apr. 14, 2014. Retrieved from <https://web.archive.org/web/20140414031038/http://www.apogeekits.com/beginner-electronic-kits/lie_detector.htm> on Jun. 14, 2017.*

Fustini, D. "Ouch! Sensing Galvanic Skin Response (GSR)". May 8, 2011. Retrieved from <https://www.element14.com/community/groups/pumping-station-one/blog/2011/05/08/ouch-sensing-galvanic-skin-response-gsr> on Jun. 14, 2017.*

International Search Report and Written Opinion of International Application No. PCT/US2015/042658 dated Oct. 29, 2015.

* cited by examiner

SHARING A SINGLE ELECTRODE BETWEEN SKIN RESISTANCE AND CAPACITANCE MEASUREMENTS

BACKGROUND

Unless otherwise indicated herein, the materials described in this section are not prior art to the claims in this application and are not admitted to be prior art by inclusion in this section.

The Galvanic skin response is a change in the conductivity and/or electrical potential of the skin due to changes in the moisture level of the skin. This change in moisture level can be caused by activation or inactivation of sweat glands in the skin. The Galvanic skin response includes the Galvanic skin resistance (GSR, and/or the related Galvanic skin conductance), a measure of the conductivity of the skin between two or more points, and the Galvanic skin potential (GSP), a measure of the voltage difference between two or more points on the skin.

SUMMARY

Some embodiments of the present disclosure provide a wearable device, including: (i) a housing; (ii) a mount configured to mount the housing to an external body surface; (iii) first and second electrical contacts protruding from the housing, wherein the first and second electrical contacts are configured to contact skin at the external body surface when the housing is mounted on the external body surface; and (iv) electronics disposed in the wearable device, wherein the electronics comprises: (a) a capacitor, wherein the capacitor has a specified capacitance; (b) an electronic switch in series with the capacitor, wherein the series combination of the capacitor and the electronic switch is electronically coupled to the first and second electrical contacts; (c) a resistance sensor configured to obtain a measurement relating to a resistance of the skin between the first and second electrical contacts when the electronic switch is closed and the wearable device is mounted to the external body surface; and (d) a capacitance sensor configured to obtain a measurement relating to a capacitance of the skin between the first and second electrical contacts when the electronic switch is open and the wearable device is mounted to the external body surface.

Some embodiments of the present disclosure present a method, including: (i) mounting a wearable device to an external body surface, wherein the wearable device comprises: (a) a housing, (b) a mount configured to mount the housing to an external body surface, (c) first and second electrical contacts protruding from the housing, (d) a capacitor having a specified capacitance, (e) an electronic switch in series with the capacitor, wherein the series combination of the capacitor and the electronic switch is electronically coupled to the first and second electrical contacts, (f) a resistance sensor configured to obtain a measurement relating to a resistance of skin between the first and second electrical contacts when the electronic switch is closed, (g) a capacitance sensor configured to obtain a measurement related to a capacitance between the first and second electrical contacts when the electronic switch is open, wherein mounting the wearable device to an external body surface comprises mounting the housing to the external body surface using the mount such that the first and second electrical contacts contact skin at the external body surface; (ii) operating, during a first period of time, the electronic switch such that the electronic switch is closed; (iii) charging, during the first period of time, the capacitor using the resistance sensor; (iv) operating, during a second period of time, the electronic switch such that the electronic switch is closed; (v) obtaining, during the second period of time, a measurement using the resistance sensor; (vi) determining a resistance of the skin between the first and second contacts based on the measurement obtained using the resistance sensor during the second period of time; (vii) operating, during a third period of time, the electronic switch such that the electronic switch is open; (viii) obtaining, during the third period of time, a measurement using the capacitance sensor; and (ix) determining a capacitance between the first and second electrical contacts based on the measurement obtained using the capacitance sensor during the third period of time.

These as well as other aspects, advantages, and alternatives, will become apparent to those of ordinary skill in the art by reading the following detailed description, with reference where appropriate to the accompanying drawings.

DETAILED DESCRIPTION

Figure 1:
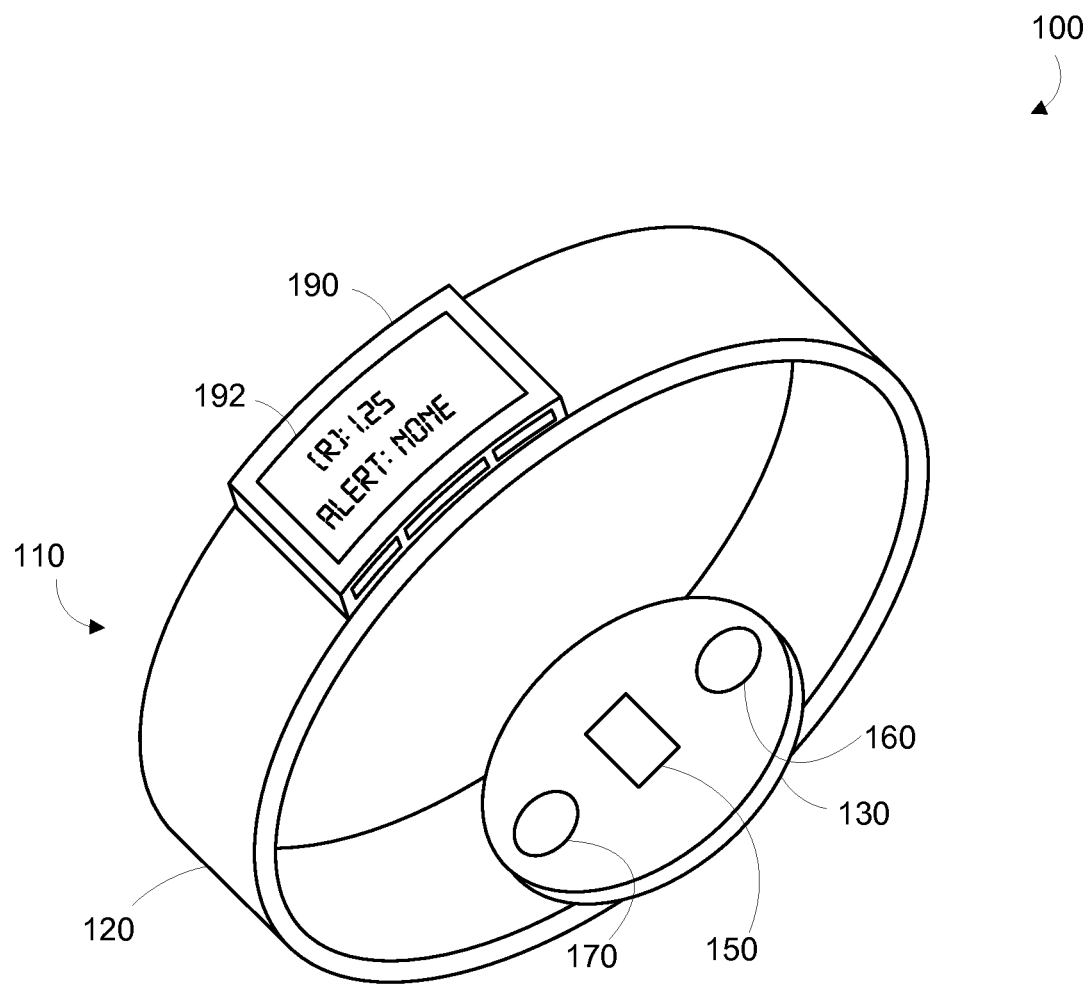
FIG. 1 is a perspective view of an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A wearable device may be configured to measure one or more physiological parameters of the wearer. The one or more physiological parameters can include skin resistance, which may be related to perspiration and, thus, the wearer's activity level, sympathetic nervous system activity, and/or emotional state/affect. To measure skin resistance, the wearable device may include two electrical contacts that protrude from a housing of the device so as to contact the wearer's skin at a location such as the wearer's wrist, forearm, upper arm, leg, thigh, etc. With the electrical contacts against the wearer's skin, electronics within the device may be used to measure an external resistance between the first and second electrical contacts. This external resistance is related to the wearer's skin resistance. The electrical contacts could additionally be employed to detect a capacitance between the first and second electrical contacts. A detected capacitance between the first and second electrical contacts could be related to one or more physiological and/or health states of the wearer. Additionally or alternatively, a detected capacitance between the first and second electrical contacts could be used to determine whether the wearable device is mounted to the wearer's skin. The wearable device could be configured to operate based on such a determination; e.g., to enter a low-power mode when the wearable device is not mounted to a wearer's skin.

In some examples, the wearable device includes a housing (e.g., a water-resistant and/or water-proof housing) and a mount (e.g., a band) that can mount the housing on a particular external body location, such as a wrist. The first and second electrical contacts may protrude from a side of the housing facing the skin at the body location, such that the first and second electrical contacts contact the skin when the housing is mounted on the body location. Electronics disposed in the housing may include a resistance sensor configured to obtain a measurement relating to the resistance of the skin at the external body surface, via the first and second electrical contacts. The electronics may additionally include a capacitor having a specified capacitance electronically combined in series with an electronic switch. The series combination of the capacitor and the electronic switch is electronically coupled to the first and second electrical contacts such that the resistance sensor or other elements of the electronics could operate to close the electronic switch and to charge the capacitor during a first period of time. The resistance sensor or other elements of the electronics could subsequently, during a second period of time, maintain the electronic switch closed and detect a temporal property of the voltage across the first and second electrical contacts (e.g., a voltage fall rate, a voltage fall time). A resistance of the skin at the external body surface could be determined based on the detected temporal property. Electronics disposed in the housing may additionally include a capacitance sensor configured to detect a capacitance between the first and second electrical contacts (e.g., by operating a relaxation oscillator to charge and subsequently discharge an equivalent capacitance between the first and second electrical contacts) when the electronic switch is open.

In some examples, the resistance sensor includes a voltage source configured to provide a specified voltage (relative to the second electrical contact), a voltage source switch coupled to the voltage source, and a resistor (having a reference resistance) connected between the voltage source switch and the first electrical contact. In this way, the voltage source can operate to charge the capacitor (e.g., to a specified voltage level) when the voltage source switch and the electronic switch are closed. Subsequently, the voltage source switch can be opened, causing the capacitor to discharge through the first and second electrical contacts. A temporal property (e.g., a voltage fall rate, a voltage fall time) of the voltage between the first and second electrical contacts when the capacitor is discharging could be related to the specific capacitance of the capacitor and the resistance of the skin at the external body surface. The resistance sensor may further include a voltage sensor configured to sense a voltage between the first and second electrical contacts directly (e.g., by being electrically coupled to the first electrical contact) or indirectly (e.g., by being electrically coupled to the first electrical contact via the resistor). In some examples, the voltage sensor includes an analog-to-digital converter that provides a digital output representative of the voltage detected by the voltage sensor.

The electronics in the housing may also include the capacitance sensor. The capacitance sensor could be configured in a variety of ways to enable the detection of a level of capacitance between the first and second electrical contacts when the electronic switch is open. In some examples, the capacitance sensor could include a relaxation oscillator configured to repeatedly charge and discharge an equivalent capacitance between the first and second electrical contacts between first and second specified voltages using specified charge and discharge currents. Such a capacitance sensor could measure an operational frequency of the relaxation oscillator, and a determined operational frequency could be used to determine a value of the capacitance between the first and second electrical contacts. Other configurations of the capacitance sensor, including capacitive bridges (i.e., one of the legs of the capacitive bridge is the equivalent capacitance between the first and second electrical contacts) and capacitive voltage dividers (i.e., a sense capacitor having a specified sense capacitance could be electrically coupled in series with the equivalent capacitance between the first and second electrical contacts) are anticipated. In some examples, the capacitance sensor could be electrically coupled to the first electrical contact through a blocking capacitor, where the blocking capacitor has a specified blocking capacitance that is much greater than an expected value of capacitance between the first and second electrical contacts (e.g., much greater than an expected skin capacitance of the skin at the external body surface).

In some examples, a capacitance value determined using the capacitance sensor could be used to determine whether the wearable device is mounted to skin of an external body surface of a wearer. For example, if a determined capacitance value is below a certain value, shows a sudden drop (e.g., is sufficiently less than a capacitance value determined during a previous time period), or satisfies some other condition, it could be determined that the wearable device is not mounted to skin of the wearer. Further, the wearable device could be operated based on such a determination; for example, the determination that the wearable device is not mounted to skin of a wearer could cause the wearable device to enter a low-power and/or sleep mode (e.g., resistance or other sensors of the wearable device, a user interface of the wearable device, or other elements of the wearable device could be deactivated and/or put into a low-power mode).

In some examples, the wearable device may include a user interface that is configured to provide user-discernible indications (e.g., visual, audible, and/or tactile indications) of one or more physiological parameters measured and/or determined by the device, such as skin resistance or skin capacitance as measured using the first and second electrical contacts. In some examples, the user interface could additionally provide a means for one or more settings of the wearable device (e.g., a frequency at which to perform skin resistance and/or capacitance measurements) to be specified by a wearer according to the wearer's preferences. In some examples, the wearable device may include a wireless communication interface that can transmit data to an external device, for example, using BLUETOOTH wireless communication, ZIGBEE wireless communication, WiFi, and/or some other wireless communication protocol. The data transmitted by the wireless communication interface may include data indicative of one or more physiological parameters measured by the device, such as skin resistance.

Note that measuring, detecting, or otherwise determining a resistance as described herein could include measuring, detecting, or otherwise determining a conductance. That is, resistance, as used herein, is defined as the inverse of conductance, such that the measurement, detection, or determination of a resistance is trivially related to the measurement, detection, or determination of a conductance. For example, a measured, detected, or otherwise determined conductance (e.g., of skin of an external body surface between two electrical contacts) could be inverted (e.g., the conductance could be raised to the −1 power, the number 1 could be divided by the conductance, or some other equivalent computation) to determine a related resistance (e.g., of skin of the external body surface between the electrical contacts). Conversely, a measured, detected, or otherwise determined resistance could be inverted to determine a related conductance.

Similarly, descriptions herein of indicating, determining some other variable or factor based on, operating a device relative to, or otherwise using a measured, detected, or otherwise determined resistance could equivalently describe such applications of a measured, detected, or otherwise determined conductance and/or of a conductance determined by inverting a resistance. Similarly, configurations, operations, and methods described herein in relation to measurement, detection, or determination of a resistance could equivalently describe the measurement, detection, or determination of a conductance and/or the determination of a resistance based on such a conductance by inverting the conductance.

II. Example Wearable Devices

A wearable device 100 can be configured to measure a skin resistance of skin at an external body surface proximate to the wearable device 100. The wearable device 100 can also be configured to measure a capacitance of the skin at the external body surface proximate to the wearable device 100. The term "wearable device," as used in this disclosure, refers to any device that is capable of being worn at, on or in proximity to an external body surface, such as a wrist, ankle, waist, chest, or other body part. A mount 110, such as a belt, wristband, ankle band, etc. can be provided to mount the device at, on or in proximity to the external body surface. In some embodiments, a mount could additionally or alternatively include an adhesive. For example, a mount could include and adhesive and could be configured such that it could be used to mount a wearable device to an external body surface of a wearer without wrapping around a part of the wearer (e.g., a limb). The mount 110 may prevent the wearable device 100 from moving relative to the body to ensure consistent contact between the wearable device 100 and the skin to enable consistent measurement of the resistance and/or capacitance of the skin. In one example, shown in FIG. 1, the mount 110, may take the form of a strap or band 120 that can be worn around a part of the body.

A housing 130 is disposed on the mount 110 such that the housing 130 can be positioned on an external surface of the body. In this position, a first electrical contact 160 and a second 170 electrical contact protruding from the housing 130 could contact skin at the external surface of the body such that the resistance and/or capacitance of the skin at the external surface of the body could be measured between the first and second electrical contacts 160, 170. Additionally or alternatively, the capacitance between the first and second electrical contacts 160, 170 could be measured when the wearable device 100 is not positioned on an external body surface of the body. In some examples, the first and second electrical contacts 160, 170 could be further configured to interface with a charger or other device such that a rechargeable battery that powers the wearable device 100 could be charged through the first and second electrical contacts 160, 170. Additionally or alternatively, such a rechargeable battery could be charged wirelessly using a coil and/or other components of the wearable device 100.

The first and second electrical contacts 160, 170 could be composed of an electrically conductive material, such as a metal or a combination of metals, or a nonmetal conductor. The first electrical contact 160 and second electrical contact 170 could be composed of the same material or different materials. The first and second electrical contacts 160, 170 could each be composed of a single material or could be composed of multiple materials. For example, the electrical contacts 160, 170 could have a bulk composed of one material and a surface plating of another material. For example, the electrical contacts 160, 170, could have a bulk composed of copper and a surface composed of gold or of gold alloyed with nickel and/or cobalt. The surface layer could be deposited by a number of methods familiar to one skilled in the art; for example, electroplating. Other compositions are possible, as well.

The first and second electrical contacts 160, 170 could be spring loaded. That is, the electrical contacts 160, 170 could be configured to include one or more springs or other elements that could be reversibly compressed. The electrical contacts 160, 170 could be spring loaded in a direction perpendicular to an external surface of the body to which the housing 130 could be mounted. That is, the electrical contacts 160, 170 could be spring loaded in order to improve and/or make more consistent an electrical connection between the electrical contacts 160, 170 and skin of the external body surface to which the housing 130 was mounted by the mount 110. Alternatively, first and second electrical contacts 160, 170 could be fixed relative to housing 130.

The geometry of the aspects of the electrical contacts 160, 170 that protrude from the housing 130 could be configured to improve and/or make more consistent an electrical connection between the electrical contacts 160, 170 and skin of the external body surface to which the housing 130 was mounted by the mount 110. For example, the protruding aspects of the electrical contacts 160, 170 could be hemispherical, conical, parabolic, cylindrical, or shaped in some other manner. The electrical contacts 160, 170 could be flat or substantially flat plates (e.g., rectangular, triangular, or other-shaped plates protruding from the housing 130). The electrical contacts 160, 170 could have a faceted geometry. For example, the electrical contacts 160, 170 could be triangular, rectangular, or other-shapes pyramids. The protruding aspects of the electrical contacts 160, 170 could have, for example, a characteristic size (e.g., diameter of cylinders, cones, or hemispheres, width of rectangular prisms or plates, or some other measure of size) between 1 and 5 millimeters. Further, the protruding aspects of the electrical contacts 160, 170 could have an inscribed, cast, and/or pressed texture or pattern. Additionally or alternatively, the exposed aspects of the electrical contacts 160, 170 could be roughened mechanically, chemically, or by some other method. Other geometries, sizes, surface treatments, and other aspects of the configuration of the electrical contacts 160, 170 are anticipated.

The electrical contacts 160, 170 could be arranged a distance apart such that a resistance and/or capacitance measured using the electrical contacts 160, 170 could have a desired property or properties. For example, the electrical contacts 160, 170 could be separated by a distance of between 1 and 50 millimeters, such as about 25 millimeters. The electrical contacts 160, 170 could be disposed on the housing 130 such that, if the housing 130 is mounted to a wrist of a wearer of the wearable device 100, the electrical contacts 160, 170 would be arranged on a line substantially parallel to the bones of the forearm of the wearer (i.e., the humerus and ulna). Other distances and directions are also possible.

The housing 130 could be configured to be water-resistant and/or water-proof. That is, the housing could be configured to include sealants, adhesives, gaskets, welds, press-fitted seams, and/or other joints such that the housing 130 was resistant to water entering an internal volume or volumes of the housing 130 when the housing 110 is exposed to water. The housing 130 could further be water-proof, i.e., resistant to water entering an internal volume or volumes of the housing 130 when the housing 130 is submerged in water. For example, the housing 130 could be water-proof to a depth of 1 meter, i.e., configured to resist water entering an internal volume or volumes of the housing 130 when the housing 130 is submerged to a depth of 1 meter. Further, the interface between the housing 130 and the first and second electrical contacts 160, 170 protruding from the housing 130 could be configured such that the combination of the housing 130 and the electrical contacts 160, 170 is water-resistant and/or water-proof The wearable device 100 includes electronics (not shown in FIG. 1) electronically coupled to the first and second electrical contacts 160, 170. The electronics are configured to measure a resistance and a capacitance of the skin at an external surface of the body proximate to the housing 130, using the first and second electrical contacts 160, 170 when the wearable device 100 is mounted to the external surface of the body.

The electronics include a capacitor and an electronic switch (e.g., a FET, a BJT, a JFET, a relay, or some other electronically-operated switching electronic element) in series with the capacitor. The series combination of the electronic switch and the capacitor is electronically coupled to the first and second electrical contacts 160, 170. Further, the electronics include a resistance sensor configured to obtain a measurement relating to the resistance of the skin between the first and second electrical contacts 160, 170 when the electronic switch is closed. For example, the resistance sensor could be configured to charge the capacitor (e.g., to a specified voltage, during a specified duration of time, using a specified current, using a specified voltage, or according to some other specified operation) during a first period of time. The resistance sensor could then be operated to sense a voltage across the capacitor at one or more points in time as the capacitor discharges through the skin at the external body surface via the first and second electrical contacts 160, 170 during a second period of time. One or more properties (e.g., a decay rate, a decay profile, a decay time to half-voltage) of the voltage across the capacitor can be related to the resistance of the skin between the first and second electrical contacts 160, 170. The one or more properties could be detected using the resistance sensor (e.g., by using an ADC to measure the voltage related to the voltage across the capacitor at one or more points in time, by detecting the output of a comparator that receives the voltage across the capacitor as an input) to determine the resistance of the skin between the first and second electrical contacts 160, 170. Further, the specified capacitance of the capacitor could be chosen to allow accurate measurement of the resistance of the skin (e.g., by having a value chosen based on an expected resistance of the skin between the first and second electrical contacts 160, 170). For example, the capacitance of the capacitor could be approximately 0.01 microfarads.

The electronics of the wearable device 100 include a capacitance sensor configured to obtain a measurement relating to the capacitance between the first and second electrical contacts 160, 170 (e.g., a capacitance of skin between the contact 160, 170) when the electronic switch is open. The capacitance sensor could be configured to apply specified currents and/or voltages to the first and second electrical contacts 160, 170 via a variety of electronic components in order to measure the capacitance. For example, the capacitance sensor could include a relaxation oscillator. That is, the capacitance sensor could include components configured to repeatedly charge and discharge an equivalent capacitance between the first and second electrical contacts 160, 170 (e.g., a capacitance of skin, air, or other substances between the first and second electrical contacts 160, 170) in a specified manner (e.g., by applying a specified charge/discharge current, by apply a specified charge/discharge voltage to the first and second electrical contacts 160, 170 via a resistor having a specified resistance) such that a frequency, a duty cycle, or some other property of the operation of the relaxation oscillator is related to the capacitance between the first and second electrical contacts 160, 170.

The wearable device 100 could be operated based on a resistance and/or capacitance detected as described herein. For example, the wearable device 100 could be configured to determine a health or other state of a wearer based on a determined resistance and/or capacitance. The wearable device 100 could be configured to determine whether the wearable device 100 is mounted to an external body surface of a wearer based on a value, a change in value, and/or some other property of a determined resistance and/or capacitance. For example, the wearable device could determine that the wearable device 100 is not mounted to a wrist of a wearer based on a detected capacitance between the electrical contacts 160, 170 being below a specified value and/or increasing or decreasing at a specified rate and/or beyond a specified minimum amount of change in determined capacitance. The wearable device 100 could be further configured to operate relative to such a determination. For example, one or more sensors (e.g., the resistance sensor) could be disabled and/or operated in a low-power state when the wearable device 100 determines, based on one or more properties of a determined capacitance as described herein, that the wearable device 100 is not mounted to skin of a wearer. Other operations relative to such a determination are anticipated.

The resistance sensor, capacitance sensor, or other elements of the wearable device 100 could be configured to prevent injury of a wearer and/or damage to the wearable device 100 due to operation of the resistance sensor and capacitance sensor to measure a resistance and capacitance, respectively, of skin at the external body surface proximate to the electrical contacts 160, 170. Clamping diodes and/or associated blocking resistors could be included in the wearable device 100 and configured to prevent voltages and/or currents above a certain specified maximum from being applied to the electrical contacts 160, 170 (and thus to the skin of the wearer) and/or to elements of the wearable device (e.g., components (e.g., an ADC) of the resistance sensor, components of a recharger coupled to the electrical contacts 160, 170). A blocking capacitor (i.e., a capacitor having a high specified value of capacitance) could be electrically disposed between one or more or the electrical contacts 160, 170 and electronics of the wearable device 100 to prevent the wearable device 100 from injuring the skin of the external body surface and/or causing electrochemical damage to the electrical contacts 160, 170 (e.g., by preventing the application of direct current to the skin for a protracted period of time, by ensuring that current injected into the skin through the electrical contacts 160, 170 is essentially balanced). Other operations and configurations of the wearable device 100 to prevent injury of a wearer and/or damage to the wearable device 100 are anticipated.

The electrical contacts 160, 170 protruding from the housing 130 could additionally be used for other purposes. For example, electronics disposed in the wearable device 100 could be used to sense an electrocardiogram (ECG) signal, a Galvanic skin potential (GSP), an electromyogram (EMG) signal, and/or some other physiological signal present at the electrical contacts 160, 170. Additionally or alternatively, the electrical contacts 160, 170 could be used to detect the presence of a charging device or some other electronic system electrically connected to the electrical contacts 160, 170. The electronics could then use the electrical contacts 160, 170 to receive electrical energy from the charging device or other system to recharge a rechargeable battery of the wearable device 100 and/or to power the wearable device 100. Such a rechargeable battery could additionally or alternatively be recharged wirelessly using electromagnetic energy received by a coil and other wireless charging circuitry disposed in the wearable device 100.

In some examples, the housing 130 further includes at least one detector 150 for detecting at least one other physiological parameter, which could include any parameters that may relate to the health of the person wearing the wearable device. For example, the detector 150 could be configured to measure blood pressure, pulse rate, respiration rate, skin temperature, etc. At least one of the detectors 150 could be configured to non-invasively measure one or more targets in blood circulating in subsurface vasculature proximate to the wearable device. In a non-exhaustive list, detector 150 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., RF, magnetic resonance) sensor.

In an example, a temperature sensor could be thermally coupled to at least one of the first and second electrical contacts 160, 170. The temperature sensor could then be operated to obtain a measurement related to a temperature of the skin at the external body surface (e.g. the external body surface proximate to the electrical contact to which the temperature sensor is thermally coupled) when the wearable device 100 is mounted to the external body surface. The temperature sensor could be thermally coupled to at least one of the first and second electrical contacts 160, 170 by a variety of methods, including but not limited to soldering or otherwise bonding the temperature sensor directly to an electrical contact, soldering or otherwise bonding the temperature sensor to a thermally conductive pad to which the electrical contact is bonded, applying a thermally conductive paste or other thermally conductive substance or element between the electrical contact and the temperature sensor, and disposing the temperature sensor within the electrical contact (e.g., within a space formed within the electrical contact). The temperature sensor could include one or more of a variety of temperature sensitive elements and/or components. For example, the temperature sensor could include one or more of a thermistor, a thermocouple, an infrared thermometer, a quartz thermometer, and a silicon bandgap temperature sensor.

The wearable device 100 may also include a user interface 190 via which the wearer of the device may receive one or more recommendations or alerts generated from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication the battery status of the device or an indication of any measured physiological parameters, for instance, a skin resistance and/or capacitance being measured by the device.

Figure 2A:
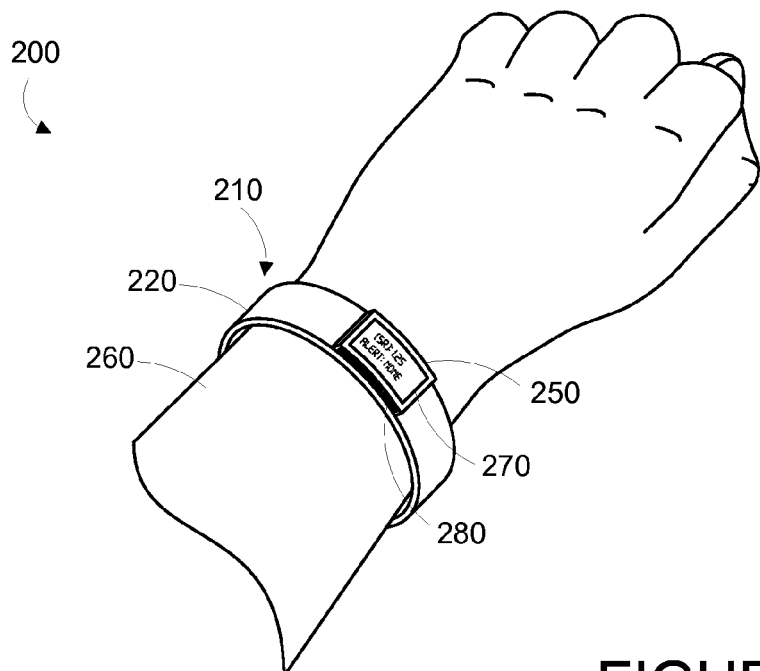
FIG. 2A is a perspective top view of an example wrist-mountable device, when mounted on a wearer's wrist.
Figure 2B:
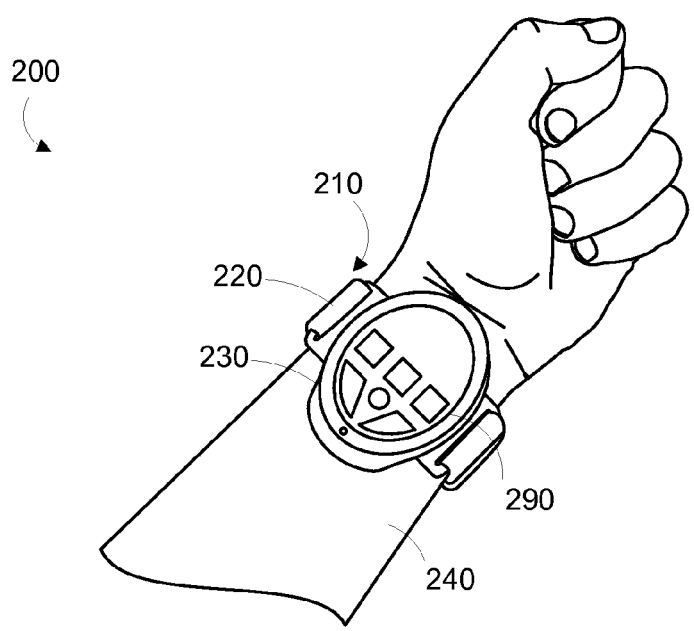
FIG. 2B is a perspective bottom view of the example wrist-mountable device shown in FIG. 2A, when mounted on a wearer's wrist.

In some examples, the wearable device is provided as a wrist-mounted device, as shown in FIGS. 2A, 2B, 3A-3C, 4A, 4B, 5 and 6. The wrist-mounted device may be mounted to a person's wrist with a wristband or cuff, similar to a watch or bracelet. As shown in FIGS. 2A and 2B, the wrist mounted device 200 may include a mount 210 in the form of a wristband 220, a housing 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts generated by the operation of the wrist mounted device 200 (for example, alerts related to a skin resistance and/or capacitance measured by the wrist mounted device 200). Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the housing 230 may be located on the anterior side 240 of the wearer's wrist. However, other configurations are contemplated.

The display 270 may be configured to display a visual indication of the alert or recommendation and/or an indication of the status of the wearable device or an indication of measured physiological parameters, for instance, the resistance and/or capacitance of the skin being measured by the wrist mounted device 200. In another example, the display 270 may be configured to display a visual indication related to a determination that the wrist mounted device is not mounted to a wrist, where the determination is based on a capacitance measured by the wrist mounted device. Further, the user interface 250 may include one or more buttons 280 for accepting inputs from the wearer. For example, the buttons 280 may be configured to change the text or other information visible on the display 270. As shown in FIG. 2B, housing 230 may also include one or more buttons 290 for accepting inputs from the wearer. The buttons 290 may be configured to accept inputs for controlling aspects of the wrist mounted device 200, such as initiating a resistance and/or capacitance measurement period or inputs indicating the wearer's current health and/or affect state (i.e., normal, anxious, angry, calm, migraine, shortness of breath, heart attack, fever, "flu-like" symptoms, food poisoning, etc.).

Figure 3A:
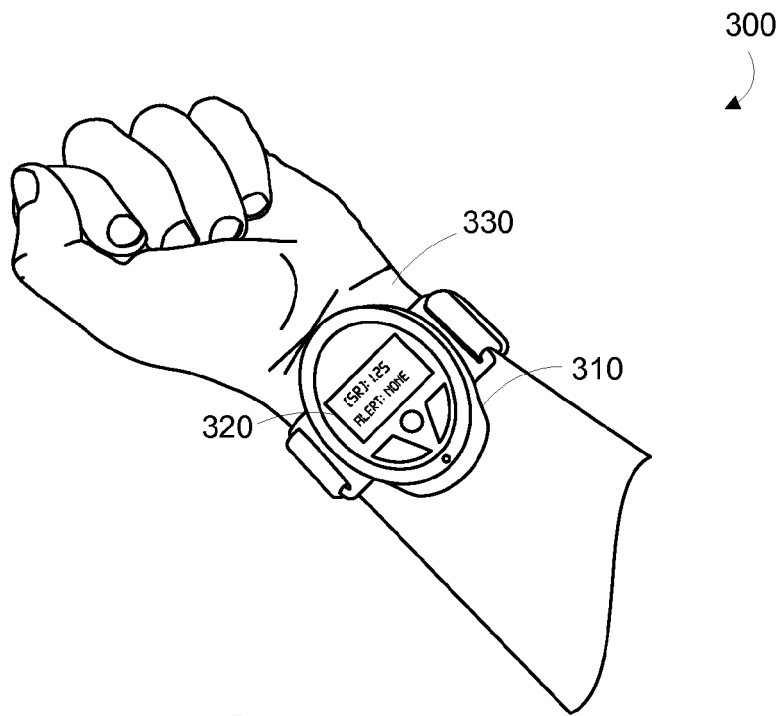
FIG. 3A is a perspective bottom view of an example wrist-mountable device, when mounted on a wearer's wrist.
Figure 3B:
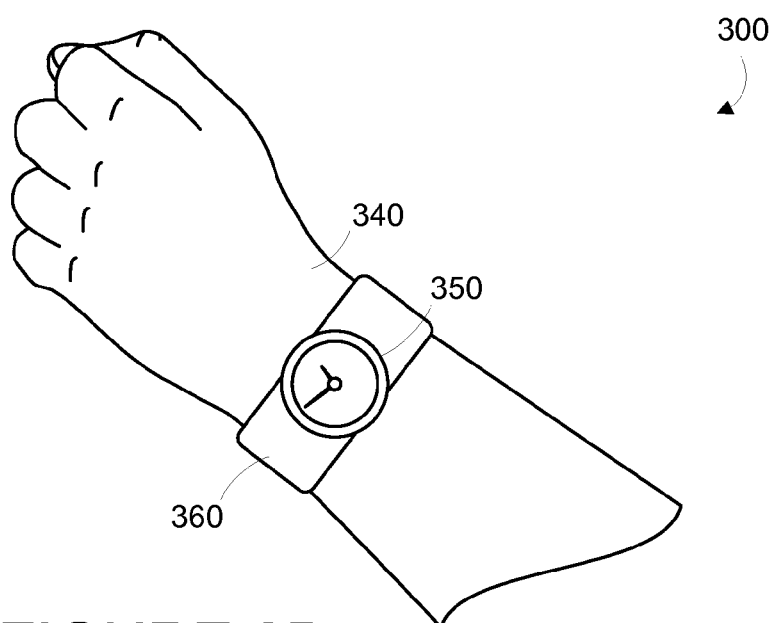
FIG. 3B is a perspective top view of the example wrist-mountable device shown in FIG. 3A, when mounted on a wearer's wrist.
Figure 3C:
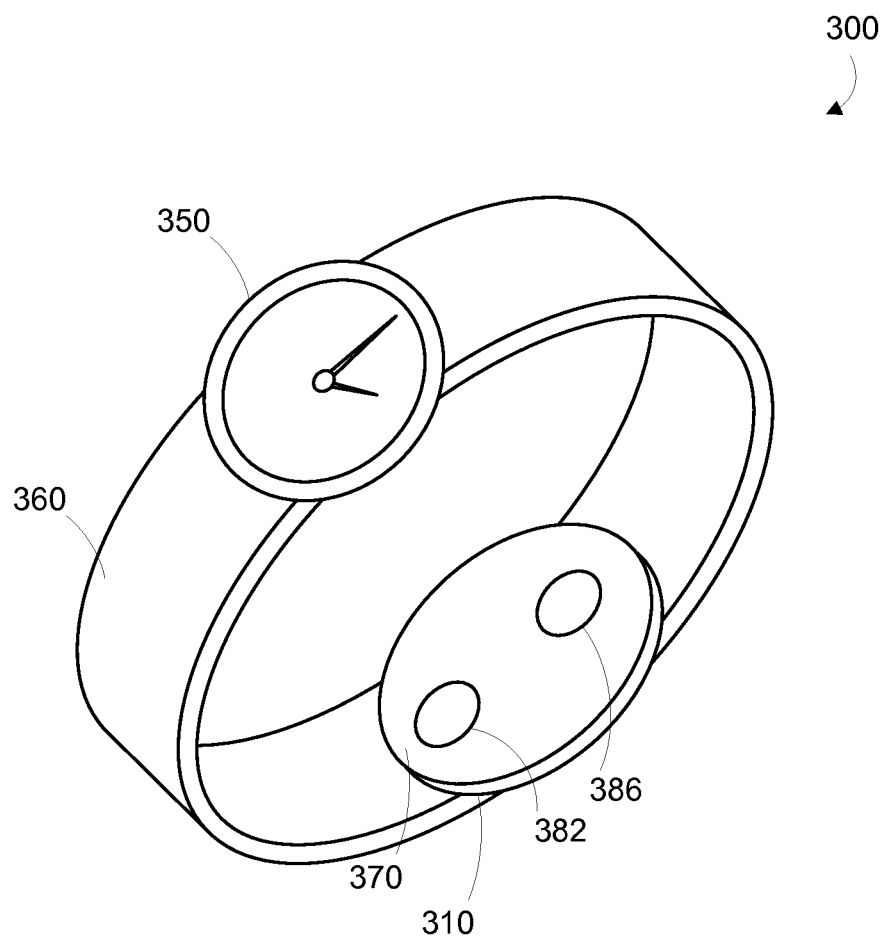
FIG. 3C is a perspective view of the example wrist-mountable device shown in FIGS. 3A and 3B.

In another example wrist-mounted device 300, shown in FIGS. 3A-3C, the housing 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the housing 310 is intended to be worn proximate to skin on an external surface of the wearer's body. A first electrical contact 382 and a second electrical contact 386 protrude from the inner face 370 of the housing 310 such that the electrical contacts 382, 386 are in stable electrical contact with skin proximate to the inner face 370 when the wrist-mounted device 300 is mounted to a wrist of a wearer. When the wrist-mounted device 300 is mounted to a wrist of a wearer as described, electronics coupled to the electrical contacts 382, 386 could measure a resistance and/or capacitance of the skin proximate to the inner face 370. When the wrist-mounted device 300 is not mounted to a wrist of a wearer, electronics coupled to the electrical contacts 382, 386 could measure a capacitance between the electrical contacts 382, 386 that could be used to determine that the wrist-mounted device 300 is not mounted to a wrist of a wearer. The electrical contacts 382, 386 could be used to enable additional functions of the wrist-mounted device 300; for example, the electrical contacts 382, 386 could also be used to charge a battery of the wrist-mounted device 300.

Figure 4A:
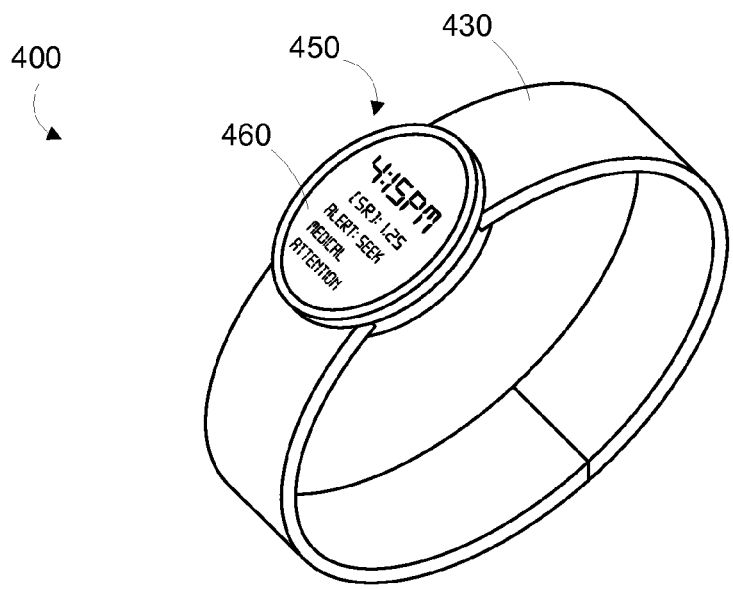
FIG. 4A is a perspective view of an example wrist-mountable device.
Figure 4B:
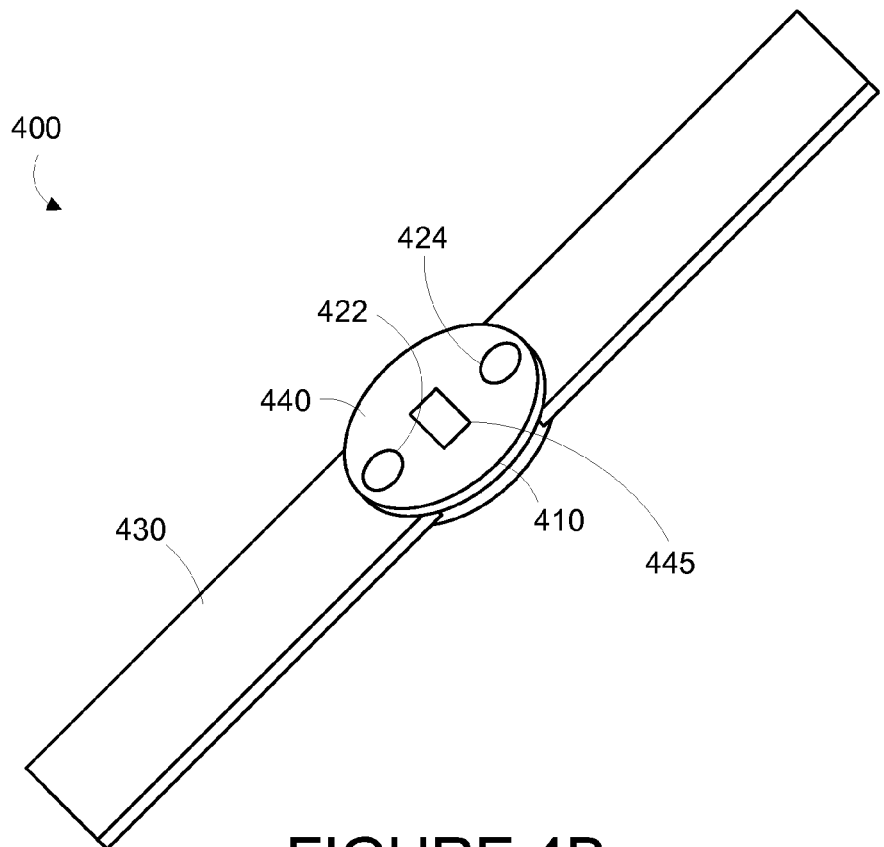
FIG. 4B is a perspective bottom view of the example wrist-mountable device shown in FIG. 4A.

In a further example shown in FIGS. 4A and 4B, a wrist mounted device 400 includes a housing 410, disposed on a strap 430. Inner face 440 of housing 410 may be positioned proximate to a body surface so that a first electrical contact 422 and a second electrical contact 424 protruding from the housing 410 may be used to measure the resistance and/or capacitance of skin of the body surface proximate to the housing 410. A detector 445 for detecting at least one other physiological parameter of the wearer could also be disposed on the inner face 440 of the housing 410. A user interface 450 with a display 460 may be positioned facing outward from the housing 410. As described above in connection with other embodiments, user interface 450 may be configured to display data about the wrist mounted device 400, including whether the wrist mounted device 400 is active, whether the wrist mounted device 400 is mounted to a wrist of a wearer (based, e.g., on a measured capacitance between the electrical contacts 422, 424), a resistance and/or capacitance of skin proximate to the inner face 440 of the housing 410 measured using the first and second electrical contacts 422, 424, physiological data about the wearer obtained using the detector 445, and one or more alerts generated by a remote server or other remote computing device, or a processor located on the wrist mounted device 400. The user interface 450 may also be configured to display the time of day, date, or other information that may be relevant to the wearer.

Figure 5:
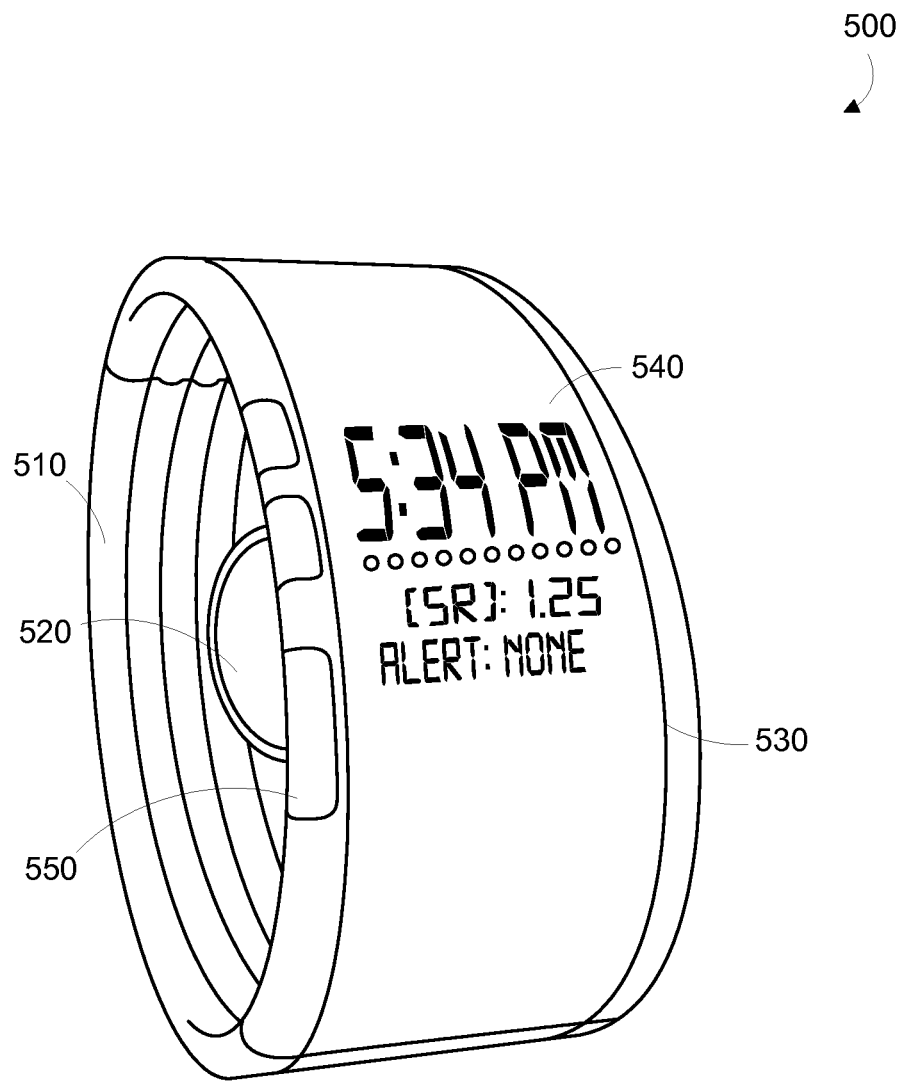
FIG. 5 is a perspective view of an example wrist-mountable device.
Figure 6:
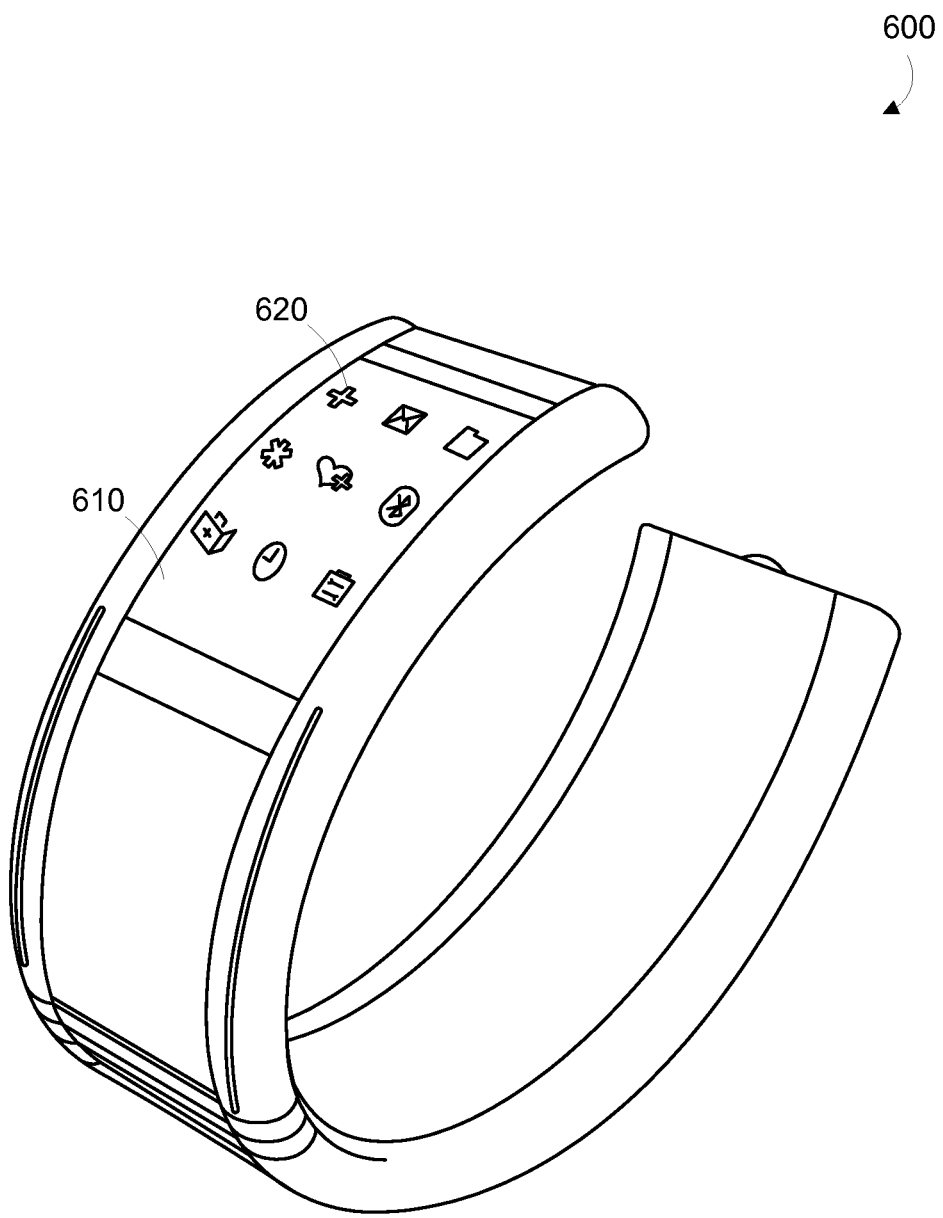
FIG. 6 is a perspective view of an example wrist-mountable device.

As shown in FIG. 5, in a further embodiment, wrist-mounted device 500 may be provided on a cuff 510. Similar to the previously discussed embodiments, device 500 includes a housing 520 and a user interface 530, which may include a display 540 and one or more buttons 550. The display 540 may further be a touch-screen display configured to accept one or more inputs by the wearer. For example, as shown in FIG. 6, display 610 may be a touch-screen configured to display one or more virtual buttons 620 for accepting one or more inputs for controlling certain functions or aspects of the device 600, or inputs of information by the user, such as current health and/or affect state.

Figure 7:
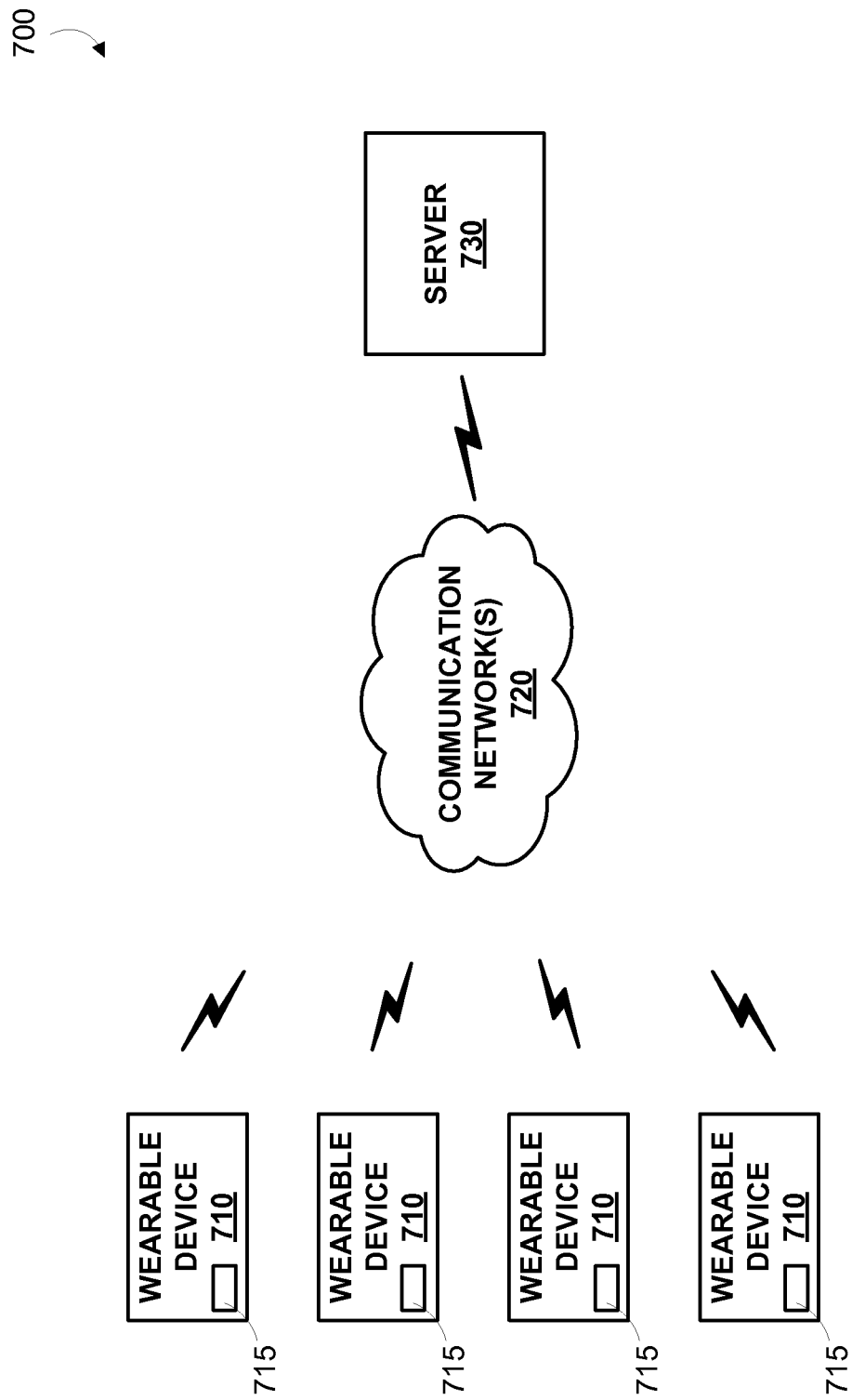
FIG. 7 is a block diagram of an example system that includes a plurality of wearable devices in communication with a server.

FIG. 7 is a simplified schematic of a system 700 including one or more wearable devices 710. The one or more wearable devices 710 may be configured to transmit data via a communication interface 715 over one or more communication networks 720 to a remote server 730. In one embodiment, the communication interface 715 includes a wireless transceiver for sending and receiving communications (e.g., indications of a measured skin resistance and/or capacitance) to and from the server 730. In further embodiments, the communication interface 715 may include any means for the transfer of data, including both wired and wireless communications. For example, the communication interface 715 may include a universal serial bus (USB) interface or a secure digital (SD) card interface. Communication networks 720 may include any of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 710 transmits data to a mobile phone or other personal computing device, which in turn transmits the data to the server 730.

In addition to receiving communications from the wearable device 710, such as data regarding health and/or affect state as input by the user or measurements of skin resistance and/or capacitance of an external surface of the body of the wearer proximate to the wearable device, the server may also be configured to gather and/or receive either from the wearable device 710 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. If measuring physiological parameters of the user (e.g., skin resistance and/or capacitance), such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

Further, some embodiments of the system may include privacy controls which may be automatically implemented or controlled by the wearer of the device. For example, where a wearer's collected data are uploaded to a cloud computing network for analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Electronics Disposed in a Wearable Device

Figure 8:
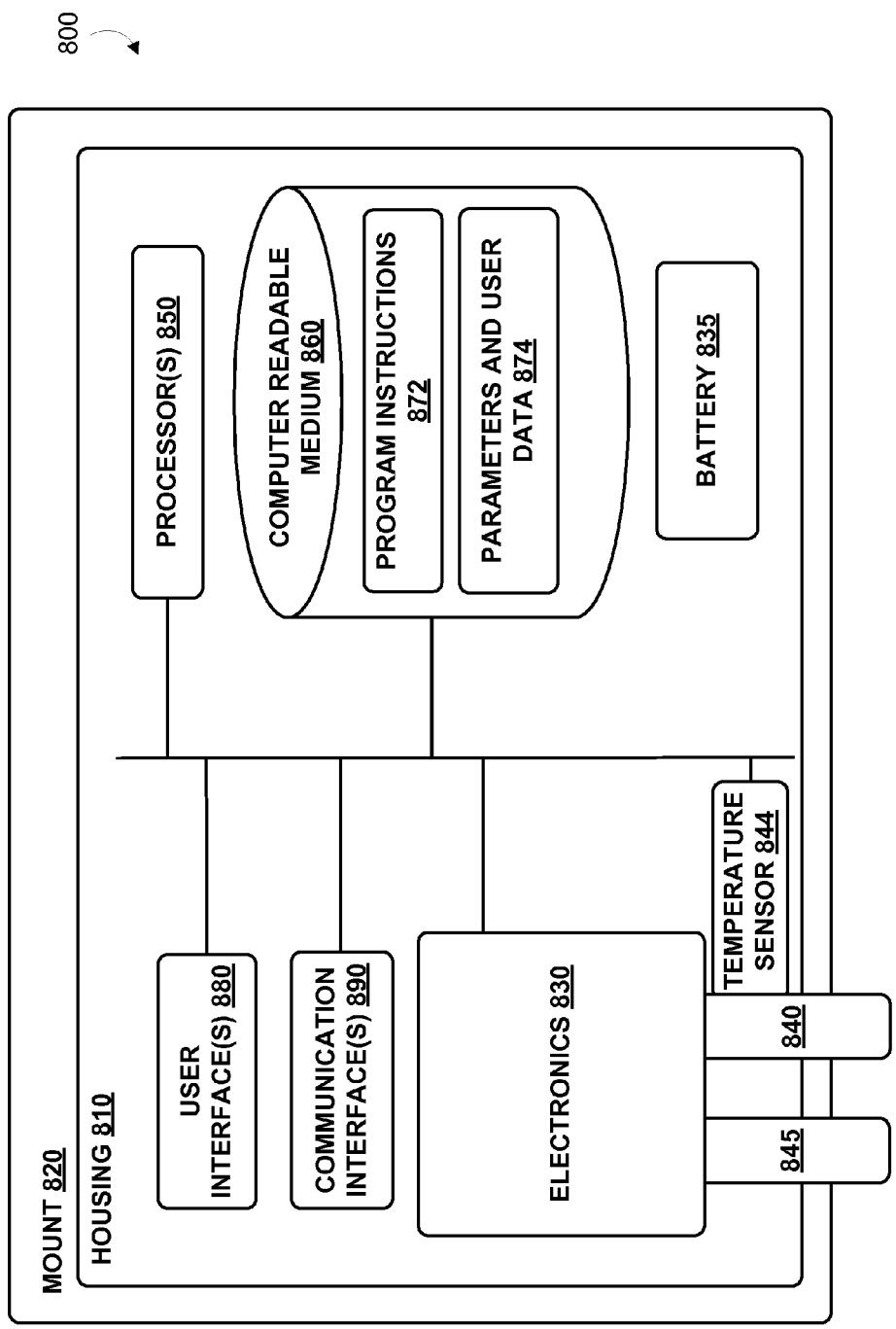
FIG. 8 is a functional block diagram of an example wearable device.

FIG. 8 is a simplified block diagram illustrating the components of a wearable device 800, according to an example embodiment. Wearable device 800 may take the form of or be similar to one of wearable device 100 and/or the wrist-mounted devices 200, 300, 400, 500, 600, shown in FIGS. 1, 2A-B, 3A-3C, 4A-4C, 5 and 6. However, wearable device 800 may also take other forms, for example, an ankle, waist, or chest-mounted device.

In particular, FIG. 8 shows an example of a wearable device 800 having a housing 810, electronics 830 for measuring a resistance of skin of an external surface of wearer proximate to the housing 810 and for measuring a capacitance (e.g., a capacitance of skin of the external body surface), a rechargeable battery 835, a user interface 880, communication interface 890 for transmitting data to a server, a temperature sensor 844, and processor(s) 850. The components of the wearable device 800 may be disposed on a mount 820 for mounting the device to an external body surface where the resistance and/or capacitance of the skin can be measured. The wearable device 800 also includes a first electrical contact 840 and a second electrical contact 845 protruding from the housing 810 and operatively coupled to the electronics 830. The electronics 830 use the first and second electrical contacts 840, 845 to measure the resistance of the skin proximate to the housing 810 and the capacitance between the electrical contacts 840, 845 (e.g., a capacitance of the skin proximate to the housing 810). The electronics could be configured to perform other functions using the first and second electrical contacts 840, 845; for example, to interface with a charger or other external device or system to power the electronics and to recharge the rechargeable battery 835. Additionally or alternatively, the rechargeable battery 835 could be charged wirelessly using a coil and/or other components of the wearable device 800 (not shown). Additionally, the temperature sensor 844 is thermally coupled to the first electrical contact 840 such that the temperature sensor 844 can be used to obtain a measurement related to the temperature of the skin proximate to the housing 810 (e.g., skin in contact with the first electrical contact 840).

Processor 850 may be a general-purpose processor or a special purpose processor (e.g., digital signal processors, application specific integrated circuits, etc.). The one or more processors 850 can be configured to execute computer-readable program instructions 872 that are stored in a computer readable medium 860 and are executable to provide the functionality of a wearable device 800 described herein.

The computer readable medium 860 may include or take the form of one or more non-transitory, computer-readable storage media that can be read or accessed by at least one processor 850. The one or more computer-readable storage media can include volatile and/or non-volatile storage components, such as optical, magnetic, organic or other memory or disc storage, which can be integrated in whole or in part with at least one of the one or more processors 850. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

The electronics 830 include a capacitor and an electronic switch (e.g., a FET, a BJT, a JFET, a relay, or some other electronically-operated switching electronic element) in series with the capacitor. The series combination of the electronic switch and the capacitor is electronically coupled to the first and second electrical contacts 845, 840. Further, the electronics 830 include a resistance sensor configured to obtain a measurement relating to the resistance of the skin between the first and second electrical contacts 845, 840 when the electronic switch is closed. For example, the resistance sensor could be configured to charge the capacitor (e.g., to a specified voltage, during a specified duration of time, using a specified current, using a specified voltage, or according to some other specified operation) during a first period of time. The resistance sensor could then be operated to sense a voltage across the capacitor at one or more points in time as the capacitor discharges through the skin at the external body surface via the first and second electrical contacts 845, 840 during a second period of time. One or more properties (e.g., a decay rate, a decay profile, a decay time to half-voltage) of the voltage across the capacitor can be related to the resistance of the skin between the first and second electrical contacts 845, 840. The one or more properties could be detected using the resistance sensor (e.g., by using an ADC to measure the voltage related to the voltage across the capacitor at one or more points in time, by detecting the output of a comparator that receives the voltage across the capacitor as an input) to determine the resistance of the skin between the first and second electrical contacts 845, 840. Further, the specified capacitance of the capacitor could be chosen to allow accurate measurement of the resistance of the skin (e.g., by having a value chosen based on an expected resistance of the skin between the first and second electrical contacts 845, 840). For example, the capacitance of the capacitor could be approximately 0.01 microfarads.

The resistance sensor could be configured in a variety of ways to allow measurement of skin resistance as described herein. For example, the resistance sensor could include a voltage source and a voltage sensor (e.g., an ADC) connected to the capacitor and/or the electronic switch. For example, the voltage source and voltage sensor could be electrically connected to the capacitor via a resistor having a specified resistance configured to, e.g., limit a charging current applied to the capacitor (e.g., a resistance of approximately 1 kilo-ohm). The voltage source could be configured to charge the capacitor during the first period of time (or according to some other operation) via a voltage source switch. For example, the voltage source switch could be operated to connect the voltage source to the capacitor during the first period of time (i.e., to charge the capacitor) and the voltage source switch could be operated to disconnect the voltage source from the capacitor during the second period of time (i.e., to allow the capacitor to discharge through the skin via the first and second electrical contacts 845, 840).

In some examples, the voltage source, voltage sensor, and other elements of the resistance sensor could be elements of a microprocessor (e.g., 850) that are electronically coupled to a pin of the microprocessor (e.g., logic gates, capacitors, high-impedance electrical switches (e.g., CMOS FETs), or other microelectronics) that is coupled to the capacitor and one of the first and second electrical contacts 845, 840 via a resistor or via some other electronic component(s). For example, the voltage source could be an internal voltage supply of the microprocessor, and the voltage source switch could be a gate of the microprocessor configured to electrically connect the internal voltage supply and/or an internal ground of the microprocessor to a pin of the microprocessor and to appear as a high impedance element when not connecting the pin to the internal voltage supply and/or the internal ground (e.g., to provide a 'three-state' digital output to the pin). An ADC of the microprocessor could additionally be configured to electrically connect to the pin.

The electronics 830 include a capacitance sensor configured to obtain a measurement relating to the capacitance between the first and second electrical contacts 845, 840 (e.g., a capacitance of skin between the contacts 845, 840) when the electronic switch is open. The capacitance sensor could be configured to apply specified currents and/or voltages to the first and second electrical contacts 845, 840 via a variety of electronic components in order to measure the capacitance. For example, the capacitance sensor could include a relaxation oscillator. That is, the capacitance sensor could include components configured to repeatedly charge and discharge an equivalent capacitance between the first and second electrical contacts 845, 840 (e.g., a capacitance of skin, air, or other substances between the first and second electrical contacts 845, 840) in a specified manner (e.g., by applying a specified charge/discharge current, by apply a specified charge/discharge voltage to the first and second electrical contacts 845, 840 via a resistor having a specified resistance) such that a frequency, a duty cycle, or some other property of the operation of the relaxation oscillator is related to the capacitance between the first and second electrical contacts 845, 840.

In a specific embodiment, the relaxation oscillator could include a voltage source configured to charge the equivalent capacitance between the electrical contacts 845, 840 via a first electronic switch and a current-limiting resistor. The relaxation oscillator could additionally include a second electronic switch configured to discharge the equivalent capacitance (e.g., by connecting the first 840 and second 845 electrical contacts together) via the current-limiting resistor. A comparator (or other voltage sensor, e.g., an ADC, a Schmitt trigger) could be operated to determine when the voltage between the electrical contacts 845, 840 has reached a first specified voltage (e.g., a first fraction of the voltage provided by the voltage source of the capacitance sensor). The first electronic switch could then be responsively opened (i.e., such that the capacitor is no longer being charged by the voltage source) and the second electronic switch could be responsively closed (i.e., such that the capacitor is being discharged). Similarly, a second comparator (or other voltage sensor, which could be the same and/or include elements in common with the first voltage sensor) could be operated to determine when the voltage between the electrical contacts 845, 840 has been reduced to a second specified voltage (e.g., a second fraction of the voltage provided by the voltage source of the capacitance sensor, where the second fraction is less than the first fraction). The second electronic switch could then be responsively opened (i.e., such that the capacitor is no longer being discharge) and the first electronic switch could be responsively closed (i.e., such that the capacitor is being charged by the voltage source). Thus, a frequency, pulse width, duty cycle, or other properties of the output(s) of the first and/or second comparators could be used to determine a property of the equivalent capacitance between the first and second electrical contacts 845, 840 (e.g., of a skin capacitance of skin between the electrical contacts 845, 840).

Additional or alternative elements and operations of the capacitance sensor are anticipated. For example, the capacitance sensor could be configured such that the equivalent capacitance between the first and second electrical contacts 845, 840 forms one leg of a capacitive and/or resistive bridge circuit that can be excited (e.g., using a specified time-varying voltage waveform) to generate an electrical signal (e.g., a voltage between and/or across elements of the capacitive bridge) that can be detected to determine the capacitance between the first and second electrical contacts 845, 840. The capacitance sensor could be connected to the first 840 and/or second 845 electrical contacts via a DC-blocking capacitor to, e.g., prevent the capacitance sensor from interfering with the use of the electrical contacts 845, 840 by the resistance sensor to measure the skin resistance or to allow some other operation(s). Such a DC-blocking capacitor could have a specified capacitance that is larger than an expected value of skin capacitance, e.g., the DC-blocking capacitor could have a capacitance of approximately 0.1 microfarads or more.

The electronics 830 could include additional components. In some examples, the electronics 830 could include a recharger configured to recharge the rechargeable battery 835 and to be powered through the electrical contacts 840, 845. In some examples, the wearable device 800 could be configured to be mounted on an external charger. The external charger could be configured to apply a voltage and/or current to the electrical contacts 840, 845 sufficient to power the recharger to recharge the rechargeable battery 835. The electronics 830 could include rectifiers, capacitors, or other elements disposed electrically between the recharger and the electrical contacts 840, 845. The rectifiers or other elements could be configured to reduce electrical interference in resistance and/or capacitance measurements made using the electrical contacts 840, 845 when the wearable device 800 is mounted to an external surface of a wearer and not mounted to an external charger. Additionally or alternatively, the wearable device 800 could include a coil and other components configured to receive electromagnetic energy (e.g., from a wireless charger) and to recharge the rechargeable battery 835 using the received electromagnetic energy. The electronics 830 could include components configured to detect an ECG, an EMG, or some other electrical signal using the electrical contacts 840, 845. The electronics 830 could include components to operate some other sensors (e.g., accelerometers, optical pulse sensors, pulse oximeters, thermometers, the temperature sensor 844) configured to detect one or more properties of a wearer of the wearable device 800 and/or of the environment of the wearable device 800.

Note that, while the electronics 830, processor(s) 850, rechargeable battery 835, and other components are described herein as being disposed in a single housing 810, other configurations are anticipated. In some examples, a wearable device could include multiple housings (e.g., the wearable devices 100, 200, 300 illustrated in FIGS. 1, 2A-B, 3A-C) and the components of the wearable device could be distributed amongst the multiple housings. For example, a first housing could contain some of the electronics 830 (for example, resistance measurement electronics, capacitance sensing electronics, temperature sensing electronics) and the electrical contacts 840, 845 could protrude from the first housing. A second housing could include the recharger electronics and the rechargeable battery 835 and elements disposed in the second housing could be electrically connected to elements disposed in the first housing. Other numbers of housings, configurations of housings, and dispositions of components within multiple housings are anticipated.

The program instructions 872 stored on the computer readable medium 860 may include instructions to perform or facilitate some or all of the device functionality described herein. For instance, program instructions 872 could include instructions to operate the electronics 830 to make a resistance and/or capacitance measurement using the electrical contacts 840, 845. The program instructions 872 could additionally include instructions to operate other elements of the electronics 830 (e.g., switches, circuit breakers, FETs) to protect other elements of the wearable device 800 that are electrically coupled to the electrical contacts 840, 845 (e.g., a resistance sensor of the electronics 830) from being damaged. The program instructions 872 could include instructions to operate based on parameter and user data 874 stored in the computer readable medium 860 and/or modify the parameters and user data 874. For example, the parameters and user data 874 could include calibration data for the wearable device 800 and/or stored resistance, temperature, and/or capacitance measurements made using the wearable device 800.

The program instructions 872 stored on the computer readable medium 860 could include instructions for operating the electronics 830 to make a resistance and/or capacitance measurement using the electrical contacts 840, 845. The instructions could include instructions to activate and/or set a value of a current source, a voltage source, a programmable resistor, an ADC, one or more electronic switches, and/or some other component(s) of the electronics 830. The instructions could include instructions to operate a voltage or current sensor to make a measurement relating to the resistance and/or capacitance. The instructions could include instructions to determine a resistance and/or capacitance based on the measurement. The instructions could further include instructions to determine the resistance and/or capacitance based on calibration or other data stored in the parameters and user data 874. The instructions could include instructions to determine whether the wearable device 800 was mounted to skin on an external surface of a wearer based on the measurement relating to the resistance and/or capacitance.

Other instructions in the program instructions 872 relating to the use of the electronics 830 to measure a resistance and/or capacitance using the electrical contacts 840, 845 are anticipated. The program instructions 872 could include instructions to make a plurality of measurements and/or determinations of the resistance and/or capacitance at a plurality of points in time using the electronics 830. The program instructions 872 could include instructions to store measurements of the resistance and/or capacitance in the parameters and user data 874 and/or later or update calibration or other data in the parameters and user data 874 based on measurements of the resistance and/or capacitance or other factors.

The instructions could include instructions to operate the wearable device 800 based on a measured or determined resistance or capacitance. For example, the instructions could describe how to determine a health or other state of a wearer based on a determined resistance and/or capacitance. The instructions could describe how to determine whether the wearable device 800 is mounted to an external body surface of a wearer based on a value, a change in value, and/or some other property of a determined resistance and/or capacitance. For example, the instructions could describe how to determine that the wearable device 800 is not mounted to a wrist of a wearer based on a detected capacitance between the electrical contacts 840, 845 being below a specified value and/or increasing or decreasing at a specified rate and/or beyond a specified minimum amount of change in determined capacitance. The instructions could further describe how to operate the wearable device 800 relative to such a determination. For example, one or more sensors (e.g., the resistance sensor) could be disabled and/or operated in a low-power state when the wearable device 800 determines, based on one or more properties of a determined capacitance as described herein, that the wearable device 800 is not mounted to skin of a wearer. Other operations relative to such a determination are anticipated and could be described by the program instructions 872.

The program instructions 872 stored on the computer readable medium 860 could include instructions for operating components of the wearable device 800 (e.g., the electronics 830) to recharge the rechargeable battery 835 and/or to power the wearable device 800 using the rechargeable battery 835. For example, the instructions could include instructions for operating switches or other electrical components to gate power from the electrical contacts 840, 845 to the recharger and/or from the recharger to the rechargeable battery 835. Additionally or alternatively, the instructions could include instructions to operate a voltage or current sensor (possibly a sensor of a resistance and/or capacitance sensor of the electronics 830) to detect the presence of an external charger in electrical contact with the electrical contacts 840, 845 and/or to detect a charge state of the rechargeable battery 835. A recharger and/or rectifier elements of the electronics 830 could be passive, that is, they could be configured to recharge the rechargeable battery 835 and/or power the wearable device 800 without direct operation by the processor(s) 850 or other elements of the wearable device 800 (other than the electrical contacts 840, 845) when the wearable device 800 is mounted to an external charger or other appropriately configured power source. Additionally or alternatively, a coil and other components of a wireless charger of the wearable device 800 could be configured to receive electromagnetic energy and to charge the rechargeable battery 835 using the received electromagnetic energy.

The program instructions 872 can include instructions for operating the user interface(s) 880. For example, the program instructions 872 could include instructions for displaying data about the wearable device 800, for displaying a measured and/or determined resistance, capacitance, and/or temperature or other information generated by the wearable device 800, or for displaying one or more alerts generated by the wearable device 800 and/or received from an external system. Further, program instructions 872 may include instructions to execute certain functions based on inputs accepted by the user interface(s) 880, such as inputs accepted by one or more buttons disposed on the user interface(s) 880.

Communication interface 890 may also be operated by instructions within the program instructions 872, such as instructions for sending and/or receiving information via an antenna, which may be disposed on or in the wearable device 800. The communication interface 890 can optionally include one or more oscillators, mixers, frequency injectors, etc. to modulate and/or demodulate information on a carrier frequency to be transmitted and/or received by the antenna. In some examples, the wearable device 800 is configured to indicate an output from the processor by modulating an impedance of the antenna in a manner that is perceivable by a remote server or other remote computing device.

In some examples, the communication interface(s) 890 could be operably coupled to the electrical contacts 840, 845 and could be configured to communicate with an external system by using the electrical contacts 840, 845. In some examples, this includes sending and/or receiving voltage and/or current signals transmitted through the electrical contacts 840, 845 when the wearable device 800 is mounted onto an external system such that the electrical contacts 840, 845 are in electrical contact with components of the external system.

In some examples, resistance measurements, capacitance measurements, temperature measurements, wearer profiles, history of wearable device use, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, resistance, temperature, and/or capacitance measurements and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by instructions contained in the program instructions 872 that a medical condition is indicated, the wearable device 800 may generate an alert via the user interface 880. The alert may include a visual component, such as textual or graphical information displayed on a display, an auditory component (e.g., an alarm sound), a tactile component (e.g., a vibration), and/or an electro-haptic component (e.g., an electro-haptic stimulus delivered using the electrical contacts 840, 845). The textual information may include one or more recommendations, such as a recommendation that the wearer of the device contact a medical professional, seek immediate medical attention, or administer a medication.

Figure 9:
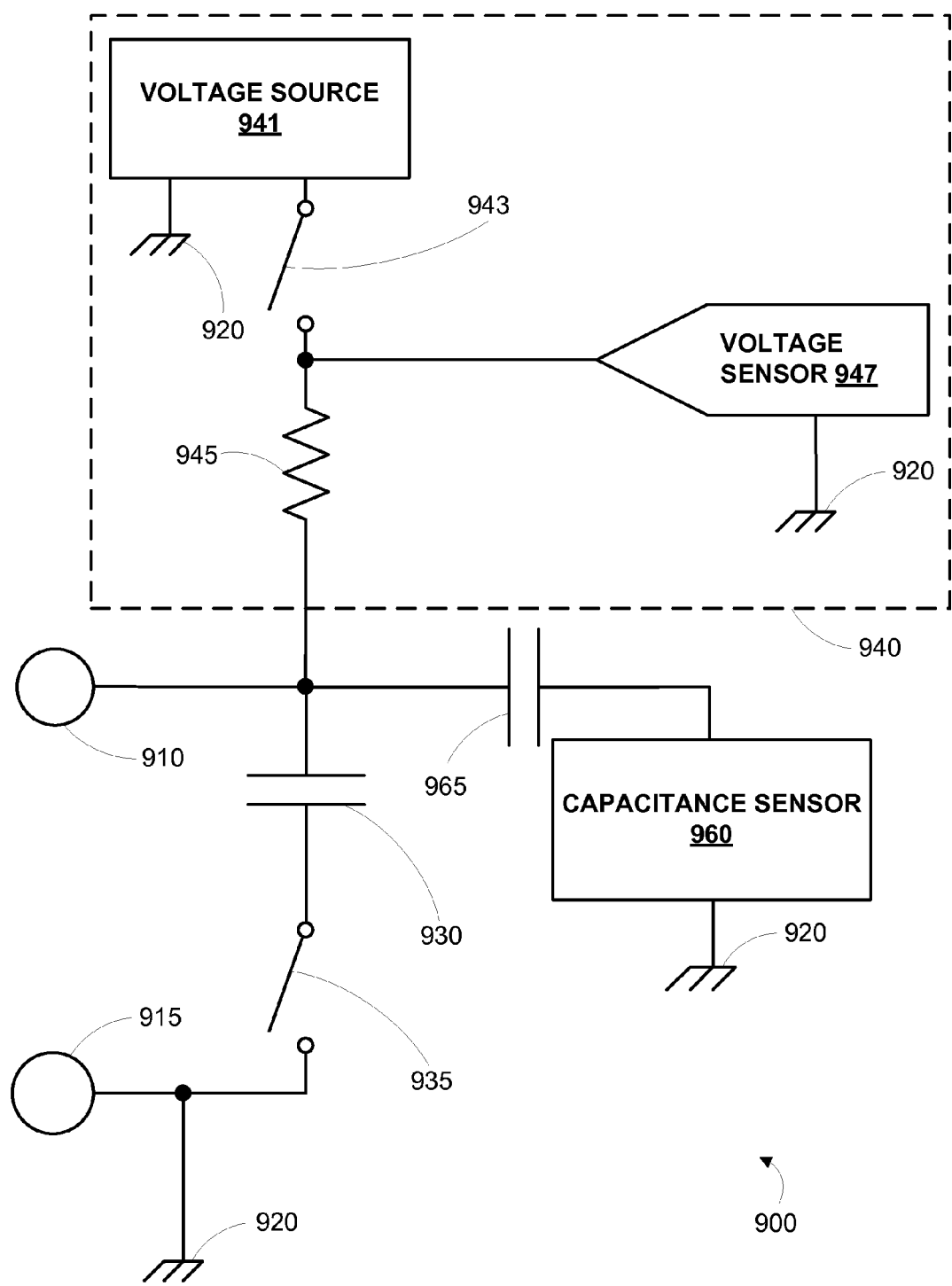
FIG. 9 is a functional block diagram of components disposed in an example wearable device.

FIG. 9 is a simplified circuit diagram of electronics 900 that could be disposed in a wearable device to measure a resistance of skin and/or measure a capacitance (e.g., a capacitance of skin) using a first electrical contact 910 and a second electrical contact 915 disposed in the wearable device. Electronics 900 are configured to include a common electrical ground 920 electrically connected to the second electrical contact 915. The electronics include a capacitor 930 connected in series with an electronic switch 935; the series combination of the capacitor 930 and the electronic switch 935 is electrically connected between the first 910 and second 920 electrical contacts. The electronics 900 include a resistance sensor 940 configured to obtain a measurement relating to the resistance of skin proximate to the first and second electrical contacts 910, 915 when the electronic switch 935 is closed. The resistance sensor 940 can include a voltage source 941, a voltage source switch 943, a resistor 945, and a voltage sensor 947. The electronics 900 also include a capacitance sensor 960 and a DC blocking capacitor 965 configured to measure a capacitance between the first and second electrical contacts 910, 915.

In the example of FIG. 9, the voltage source 941 is electrically connected to the first electrical contact 910 through the voltage source switch 943 and the resistor 935. Additionally, the voltage sensor 947 has an input electrically connected to the first electrical contact 910 through the resistor 945. Further, at least the reference voltage source 941, voltage sensor 947, capacitance sensor 960, and electronic switch 935 are electrically connected to the common electrical ground 920 that is electrically connected to the second electrical contact 915.

Electronics 900 could be disposed in a wearable device (e.g., the wearable devices 100, 200, 300, 400, 500, 600, 710, 800 illustrated in FIGS. 1, 2A-B, 3A-C, 4A-B, 5, 6, 7, and 8). Individual elements of the electronics 900 could be embodied as respective discrete components. Additionally or alternatively, one or more elements of the electronics 900 could be incorporated into one or more integrated circuits. In examples where the electronics 900 are included in a wearable device composed of multiple housings or other subassemblies, the elements of the electronics 900 could all be disposed in a single housing or subassembly or elements of the electronics 900 could be disposed in multiple housings or subassemblies and connected using wires, cables, or other means passing between housings or subassemblies.

Obtaining a measurement relating to the resistance of skin at an external body surface proximate to the first and second electrical contacts 910, 915 can include operating the resistance sensor 940 to charge the capacitor 930 (e.g., to a specified voltage, during a specified duration of time, using a specified current, using a specified voltage, or according to some other specified operation) during a first period of time when the electronic switch 935 is closed. This could include closing the voltage source switch 943 during the first period of time such that the voltage source 941 charges the capacitor 930 via the resistor 945 at a rate (i.e., with a current) related to at least the capacitance of the capacitor 930, the resistance of the resistor 945, and a difference between the voltage provided by the voltage source 941 and the voltage across the capacitor 930. The resistance sensor could then be operated to sense a voltage across the capacitor at one or more points in time as the capacitor discharges through the skin at the external body surface via the first and second electrical contacts 910, 915 during a second period of time when the electronic switch 935 is closed. This could include opening the voltage source switch 943 during the second period of time such that the capacitor 930 discharges through the electrical contacts 910, 915. One or more properties (e.g., a decay rate, a decay profile, a decay time to half-voltage) of the voltage across the capacitor can be related to the resistance of the skin between the first and second electrical contacts 910, 915. The one or more properties could be detected using the resistance sensor (e.g., by using an ADC of the voltage sensor 947 to measure the voltage related to the voltage across the capacitor at one or more points in time, by detecting the output of a comparator and/or Schmitt trigger of the voltage sensor 947 that receives the voltage across the capacitor as an input) to determine the resistance of the skin between the first and second electrical contacts 910, 915. Further, the specified capacitance of the capacitor could be chosen to allow accurate measurement of the resistance of the skin (e.g., by having a value chosen based on an expected resistance of the skin between the first and second electrical contacts 910, 915). For example, the capacitance of the capacitor could be approximately 0.01 microfarads.

The voltage sensor 947 could be part of a microcontroller disposed in a wearable device. The voltage sensor 947 could be configured as a discrete component disposed in a wearable device. The voltage sensor 947 could be operated by a microcontroller or other processor(s) to make a measurement of a voltage related to the voltage between the first and second electrical contacts 910, 915. The voltage sensor 947 could include one or more comparators, Schmitt triggers, direct-conversion ADCs, successive-approximation ADCs, sigma-delta ADCs, or some other type(s) of ADC. The voltage sensor 947 could include an amplifier, a filter, a sample-and-hold, and/or some other components.

In some examples, the voltage source 941, voltage sensor 947, voltage source switch 943, and/or other elements of the resistance sensor 940 could be elements of a microprocessor that are electronically coupled to a pin of the microprocessor (e.g., logic gates, capacitors, high-impedance electrical switches (e.g., CMOS FETs), or other microelectronics) that is coupled to the capacitor 930 and the first electrical contact 910 via the resistor 945 or via some other electronic component(s). For example, the voltage source 941 could be an internal voltage supply of the microprocessor, and the voltage source switch 943 could be a gate of the microprocessor configured to electrically connect the internal voltage supply and/or an internal ground of the microprocessor (e.g., an internal ground electrically connected to the common electrical ground 920) to a pin of the microprocessor and to appear as a high impedance element when not connecting the pin to the internal voltage supply and/or the internal ground (e.g., to provide a 'three-state' digital output to the pin). An ADC of the microprocessor could additionally be configured to electrically connect to the pin and to act as the voltage sensor 947.

The voltage sensor 947 could be used to measure a voltage relating to a resistance of skin proximate to the electrical contacts 910, 915. The voltage sensor 947 could also be used to detect other signals. In some examples, the voltage 947 sensor could be used to detect whether the electrical contacts 910, 915 are in contact with skin proximate to the electrical contacts 910, 915. Additionally or alternatively, the voltage sensor could be used to detect when an external charger or other power source was connected to the first and second electrical contacts 910, 915 and/or a charge state of a rechargeable battery connected to the electronics 900. Other uses of the voltage sensor are anticipated.

The resistance sensor 940 could include additional and/or alternate circuitry than that disclosed above. The resistance sensor 940 could include linear and nonlinear filtering circuitry and/or voltage isolation circuitry. For example, the resistance sensor 940 could include clamping diodes, blocking resistors, blocking capacitors, electronic switches, or other elements configured to prevent components of the resistance sensor 940 from being damaged by voltages and/or currents at/through the electrical contacts 910, 915. The resistance sensor 940 could include one or more analog components or functional blocks. The resistance sensor 940 could include analog electronics to perform some analog calculation and/or filtering based on a measured voltage or other signal; the results of this analog calculation and/or filtering could be used to perform some function or could be digitized for use by a processor or microcontroller.

The voltage source 941 could be any component configured to provide a stable, specified voltage relative to a common electrical ground 920. For example, the voltage source 941 could include a forward or reverse biased Zener diode, germanium diode, silicon diode, and/or avalanche diode. The voltage source 941 could additionally or alternatively include a bandgap voltage reference. The voltage source 941 could be temperature stabilized. In some examples, a voltage provided by the voltage source could be adjustable, for example by a microcontroller connected to the reference voltage source. The voltage source 941 could be an internal voltage provided by a microcontroller.

The resistor 945 could be any electronic component having a stable reference resistance value. For example, the resistor could be a thin-film resistor, a thick-film resistor, a laser-trimmed resistor, a wire-wound resistor, or some other type of resistive element. The resistor 945 could be an element of a microcontroller. In some examples, the resistor 945 could have an adjustable resistance, and the adjustable resistance could be controlled by e.g. a microcontroller. In some examples, the resistor 945 could have a resistance of approximately 1 kilo-ohm.

The electronic switch 935 and voltage source switch 943 could be any component that can be operated to allow substantially no current to flow through itself during a first period of time and to allow current to flow substantially unimpeded (i.e., to have a very low resistance) during a second period of time. The switches 935, 943 could include a FET, a MOSFET, a BJT, an IGBT, or some other switchable electronic component. The switches 935, 943 could be configured to contact a heat sink or other heat management component to reduce the temperature of the switches 935, 943 during operation. The switches 935, 943 could be configured (e.g., could have a wide and/or or deep channel, gate, or other semiconductor feature) to have a very low 'on'-resistance (e.g., on the order of milli-ohms), a very low gate capacitance, or some other specified properties according to an application.

The electronics 900 include a capacitance sensor 960 configured to obtain a measurement relating to the capacitance between the first and second electrical contacts 910, 915 (e.g., a capacitance of skin between the contacts 910, 915) via the DC blocking capacitor 965 when the electronic switch 935 is open. The capacitance sensor 960 could be configured to apply specified currents and/or voltages to the first and second electrical contacts 910, 915 via a variety of electronic components in order to measure the capacitance. For example, the capacitance sensor 960 could include a relaxation oscillator. That is, the capacitance sensor could include components configured to repeatedly charge and discharge an equivalent capacitance between the first and second electrical contacts 910, 915 (e.g., a capacitance of skin, air, or other substances between the first and second electrical contacts 910, 915) in a specified manner (e.g., by applying a specified charge/discharge current, by apply a specified charge/discharge voltage to the first and second electrical contacts 910, 915 via a resistor having a specified resistance) such that a frequency, a duty cycle, or some other property of the operation of the relaxation oscillator is related to the capacitance between the first and second electrical contacts 910, 915.

The capacitance sensor 960 could be connected to the first 910 electrical contact via the DC-blocking capacitor 965 to, e.g., prevent the capacitance sensor 960 from interfering with the use of the electrical contacts 910, 915 by the resistance sensor 940 to measure the skin resistance or to allow some other operation(s). The DC-blocking capacitor 965 could have a specified capacitance that is larger than an expected value of skin capacitance, e.g., the DC-blocking capacitor 965 could have a capacitance of approximately 0.1 microfarads or more. In some examples, the DC blocking capacitor 965 could be omitted, and the capacitance sensor 960 could be connected directly to the first electrical contact 910. In some examples, the electronics 900 could additionally or alternatively include a DC blocking capacitor connected between the capacitance sensor 960 and the common electrical ground 920.

In a specific embodiment, the relaxation oscillator could include a voltage source configured to charge the equivalent capacitance between the electrical contacts 910, 915 via a first electronic switch and a current-limiting resistor. The relaxation oscillator could additionally include a second electronic switch configured to discharge the equivalent capacitance (e.g., by connecting the first 910 and second 915 electrical contacts together) via the current-limiting resistor. A comparator (or other voltage sensor, e.g., an ADC, a Schmitt trigger) could be operated to determine when the voltage between the electrical contacts 910, 915 has reached a first specified voltage (e.g., a first fraction of the voltage provided by the voltage source of the capacitance sensor 960). The first electronic switch could then be responsively opened (i.e., such that the capacitor is no longer being charged by the voltage source) and the second electronic switch could be responsively closed (i.e., such that the capacitor is being discharged). Similarly, a second comparator (or other voltage sensor, which could be the same and/or include elements in common with the first voltage sensor) could be operated to determine when the voltage between the electrical contacts 910, 915 has been reduced to a second specified voltage (e.g., a second fraction of the voltage provided by the voltage source of the capacitance sensor 960, where the second fraction is less than the first fraction). The second electronic switch could then be responsively opened (i.e., such that the capacitor is no longer being discharge) and the first electronic switch could be responsively closed (i.e., such that the capacitor is being charged by the voltage source). Thus, a frequency, pulse width, duty cycle, or other properties of the output(s) of the first and/or second comparators could be used to determine a property of the equivalent capacitance between the first and second electrical contacts 910, 915 (e.g., of a skin capacitance of skin between the electrical contacts 910, 915).

Additional or alternative elements and operations of the capacitance sensor 960 are anticipated. For example, the capacitance sensor 960 could be configured such that the equivalent capacitance between the first and second electrical contacts 910, 915 forms one leg of a capacitive and/or resistive bridge circuit that can be excited (e.g., using a specified time-varying voltage waveform) to generate an electrical signal (e.g., a voltage between and/or across elements of the capacitive bridge) that can be detected to determine the capacitance between the first and second electrical contacts 910, 915.

The electronics 900 could be configured and/or could include additional components to perform additional functions to those described above. In some examples, the electronics 900 could include a recharger configured to receive electrical energy through the electrical contacts 910, 915 and to charge a rechargeable battery and/or power the electronics 900 using the received electrical energy. In some examples, the voltage sensor 947 could be operated to determine a type and/or capacity of a charger electrically connected to the electrical contacts 910, 915. In some examples, the voltage sensor 947 could be operated to receive communications from an external device that is configured to be connected to the electrical contacts 910, 915 and to transmit information to the electronics 900 by modulating a voltage waveform presented to the electrical contacts 910, 915. In some examples, the electronics 900 could be configured to measure other physiological properties of a wearer of a device including the electronics 900. For example, the voltage sensor 947 could be configured to sense a Galvanic skin potential, an electrocardiogram (ECG), an electromyogram (EMG), and/or other signals and/or properties of a wearer by using the electrical contacts 910, 915. Other configurations and applications of the electronics 900 and of wearable devices or other systems including the electronics 900 are anticipated.

IV. Illustrative Methods for Operating a Wearable Device

Figure 10:
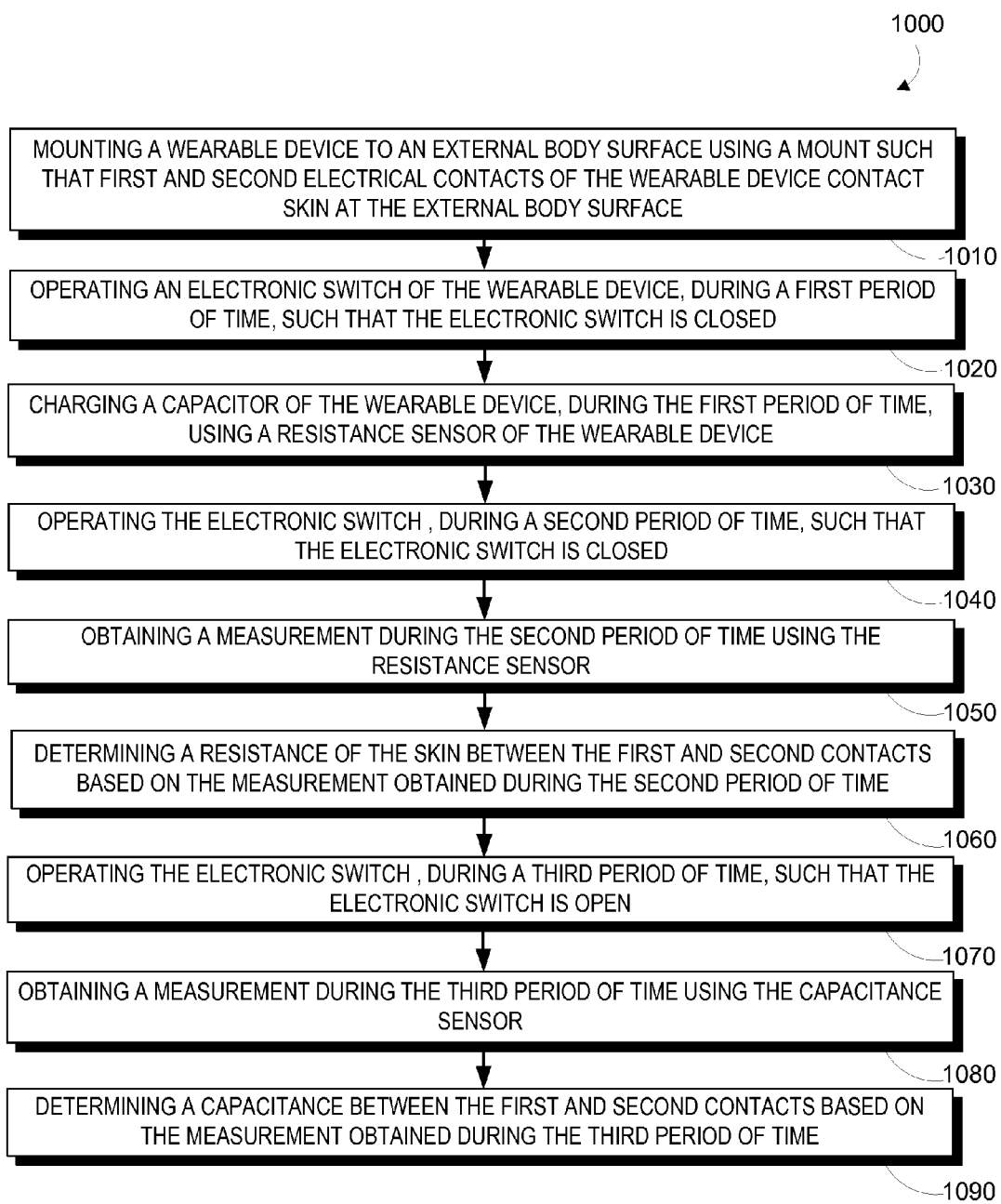
FIG. 10 is a flowchart of an example method.

FIG. 10 is a flowchart of a method 1000 for operating a wearable device. The operated wearable device includes (i) a housing, (ii) a mount configured to mount the housing to an external body surface, (iii) first and second electrical contacts protruding from the housing, (iv) a capacitor having a specified capacitance, (v) an electronic switch in series with the capacitor, wherein the series combination of the capacitor and the electronic switch is electronically coupled to the first and second electrical contacts, (vi) a resistance sensor configured to obtain a measurement relating to a resistance of skin via the first and second electrical contacts when the electronic switch is closed, and (vii) a capacitance sensor configured to obtain a measurement related to a capacitance between the first and second electrical contacts when the electronic switch is open.

The method 1000 includes mounting the wearable device to an external body surface using the mount such that the first and second electrical contacts contact skin at the external body surface (1010). In some examples, the wearable device could be configured to be mounted to a wrist of a wearer (e.g., the embodiments illustrated in FIGS. 1, 2A-B, 3A-C, 4A-B, 5, and 6) such that the first and second electrical contacts were in contact with skin of the wrist of the wearer. In some examples, the mount includes an adhesive, and mounting the wearable device to an external body surface (1010) includes activating, applying, and/or exposing the adhesive and adhering the wearable device to the external body surface.

The method 1000 also includes operating the electronic switch, during a first period of time, such that the electronic switch is closed (1020). This could include applying a specified voltage, current, or other electrical signal to the electronic switch such that the electronic switch has a very small effective resistance to the flow of current (e.g., the electronic switch has a very low effective resistance, e.g., a few tens of milliohms). In some examples, the electronic switch could be a FET, a BJT, or some other transistor elements and operating the electronic switch 1020 could include applying a high voltage (e.g., a voltage provided by a power supply of the wearable device), a low voltage, or a substantially zero voltage to a gate, base, or other control terminal of the electronic switch.

The method 1000 also includes charging the capacitor, during the first period of time, using the resistance sensor (1030). This could include applying a specified voltage, current, or other electrical energy to the capacitor. This could include applying a specified electrical energy to the capacitor for a specified duration of time. This could include charging the capacitor until the voltage on the capacitor had reached a specified level (e.g., a specified fraction of a voltage provided by a power supply of the wearable device). For example, a voltage could be applied, through a current-limiting resistor, to the capacitor, and the voltage across the capacitor could be measured by a comparator, Schmitt trigger, and/or ADC. When the comparator, Schmitt trigger, and/or ADC indicated that the voltage across the capacitor had reached the specified voltage, the voltage source could be responsively operated to cease charging the capacitor.

The method 1000 also includes operating the electronic switch, during a second period of time, such that the electronic switch is closed (1040). This could include applying a specified voltage, current, or other electrical signal to the electronic switch such that the electronic switch has a very small effective resistance to the flow of current (e.g., the electronic switch has a very low effective resistance, e.g., a few tens of milliohms). In some examples, the electronic switch could be a FET, a BJT, or some other transistor elements and operating the electronic switch 1040 could include applying a high voltage (e.g., a voltage provided by a power supply of the wearable device), a low voltage, or a substantially zero voltage to a gate, base, or other control terminal of the electronic switch.

The method 1000 also includes obtaining a measurement, during the second period of time, using the resistance sensor (1050). For example, the resistance sensor could include a voltage sensor (e.g., an ADC, a comparator, a Schmitt trigger) configured to generate a measurement related to the voltage across the capacitor. The voltage sensor could include an ADC, and the ADC could be operated to measure a voltage at one or more points in time during the second period of time. The voltage sensor could include a comparator configured to indicate whether the voltage across the capacitor is above or below a specified voltage, and a time at which the output of the comparator changes relative to the first and second periods of time could be measured.

The method 1000 also includes determining a resistance of the skin between the first and second electrical contacts based on the measurement obtained during the second period of time (1060). In some examples, a processor or other system disposed in the wearable device could operate a voltage sensor included in the resistance sensor to measure the voltage between the first electrical contact and the second electrical contact at one or more points in time during the second period of time. The processor could then execute instructions such that a resistance of the skin was determined based a decay rate, a decay profile, a decay time to half-voltage, or some other property of the voltage across the capacitor as the capacitor discharges through the skin via the electrical contacts during the second period of time. Determining the resistance of the skin at the external body surface based on the measurement obtained during the second period of time (1060) could include determining a multiple of a specified capacitance of the capacitor. The determined multiple could correspond to a time property (e.g., a decay rate, a decay profile, a decay time to half-voltage) of the measurement(s) obtained during the second period of time. Other methods of determining the resistance of the skin based on the measurement obtained during the second period of time 1060 are anticipated.

The method 1000 also includes operating the electronic switch, during a third period of time, such that the electronic switch is open (1070). This could include applying a specified voltage, current, or other electrical signal to the electronic switch such that the electronic switch has a very large effective resistance to the flow of current (e.g., the electronic switch has a very high effective resistance, e.g., a few tens of mega-ohms). In some examples, the electronic switch could be a FET, a BJT, or some other transistor elements and operating the electronic switch 1070 could include applying a high voltage (e.g., a voltage provided by a power supply of the wearable device), a low voltage, or a substantially zero voltage to a gate, base, or other control terminal of the electronic switch.

The method 1000 also includes obtaining a measurement, during the third period of time, using the capacitance sensor (1080). For example, the capacitance sensor could include a relaxation oscillator configured to generate an output having one or more properties (e.g., a frequency, a duty cycle, a pulse width) related to the capacitance between the electrical contacts (e.g., a capacitance of skin between the electrical contacts). The capacitance sensor could include comparators, current sources, voltage sources, or other elements as described herein and configured to generate an electrical output having one or more properties related to the capacitance between the electrical contacts.

The method 1000 also includes determining a capacitance between the first and second electrical contacts (e.g., a capacitance of skin between the electrical contacts) based on the measurement obtained during the third period of time (1090). In some examples, a processor or other system disposed in the wearable device could operate to measure a frequency, a pulse width, a duty cycle, or some other properties of an electrical output of the capacitance sensor at one or more points in time during the third period of time. The processor could then execute instructions such that a capacitance between the electrical contacts was determined based on the properties of the electrical output(s) of the capacitance sensor during the third period of time. Determining the capacitance between the electrical contacts based on the measurement obtained during the third period of time (1090) could include determining a capacitance based on a lookup table or other calibration data relating values of the electrical output(s) of the capacitance sensor (e.g., a frequency, pulse width, duty cycle, or other temporal properties of an output waveform) to values of capacitance. Other methods of determining the capacitance between the electrical contacts based on the measurement obtained during the third period of time 1090 are anticipated.

The method 1000 for operating a wearable device could include additional steps relating to a determined resistance and/or capacitance. In some examples, the method 1000 could include indicating the determined resistance and/or capacitance using a display disposed in the wearable device. In some examples, the method 1000 could include wirelessly indicating the determined resistance and/or capacitance using a wireless transmitter disposed in the wearable device. For example, the wearable device could indicate a determined resistance and/or capacitance or sequence of such to a remote system (e.g., a server or cloud service accessible to a healthcare provider). In some examples, the method 1000 could include operating the wearable device based on the determined resistance and/or capacitance. For example, the wearable device could be operated to generate an alert, send a transmission to a remote system, or some other action in response to a determined resistance and/or capacitance or sequence of such (e.g., if the determined resistance or capacitance exceeds a threshold). In another example, the method 100 could include determining whether the wearable device is mounted to an external body surface of a wearer based on a value, a change in value, and/or some other property of a determined resistance and/or capacitance. For example, the method could include determining that the wearable device is not mounted to a wrist of a wearer based on a detected capacitance between the electrical contacts being below a specified value and/or increasing or decreasing at a specified rate and/or beyond a specified minimum amount of change in determined capacitance. The method could further include operating the wearable device relative to such a determination. For example, one or more sensors (e.g., the resistance sensor) could be disabled and/or operated in a low-power state responsive to a determination, based on one or more properties of a determined capacitance as described herein, that the wearable device is not mounted to skin of a wearer. Other applications of a determined resistance and/or capacitance are anticipated.

The example method 1000 illustrated in FIG. 10 is meant as an illustrative, non-limiting example. Additional or alternative elements of the method and additional or alternative components of the wearable device are anticipated, as will be obvious to one skilled in the art.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A wearable device, comprising:
   a housing;
   first and second electrical contacts protruding from the housing, wherein the first and second electrical contacts contact skin at an external body surface when the housing is mounted on the external body surface; and
   electronics disposed in the wearable device, wherein the electronics comprises:
      a capacitor, wherein the capacitor has a specified capacitance;
      an electronic switch in series with the capacitor, wherein the first and second electrical contacts are electronically coupled together via the series combination of the capacitor and the electronic switch;
      a resistance sensor electronically coupled to the second electrical contact via the series combination of the capacitor and the electronic switch, wherein the resistance sensor obtains a measurement relating to a resistance of the skin between the first and second electrical contacts when the electronic switch is closed and the wearable device is mounted to the external body surface; and
      a capacitance sensor electronically coupled to the second electrical contact via the series combination of the capacitor and the electronic switch and in parallel with the resistance sensor, wherein the capacitance sensor obtains a measurement relating to a capacitance of the skin between the first and second electrical contacts when the electronic switch is open and the wearable device is mounted to the external body surface.

2. The wearable device of claim 1, wherein the external body surface is a wrist location.

3. The wearable device of claim 1, wherein the resistance sensor comprises:
   a voltage source that provides a specified voltage relative to the second electrical contact;
   a voltage source switch coupled to the voltage source;
   a resistor connected between the voltage source switch and the first electrical contact, wherein the resistor has a specified resistance; and
   a voltage sensor coupled to the resistor, wherein the voltage sensor senses a voltage between the first and second electrical contacts via the resistor, and wherein the voltage is related to at least the specified voltage, the specified resistance, and the resistance of the skin between the first and second electrical contacts.

4. The wearable device of claim 3, wherein the voltage sensed by the voltage sensor when the housing is mounted on the external body surface decreases over time in accordance with a decay profile when the voltage source switch is open and the electronic switch is closed, and wherein the decay profile is related to the resistance of the skin between the first and second electrical contacts and the specified capacitance.

5. The wearable device of claim 1, further comprising a user interface that provides a user-discernible indication of the resistance of the skin between the first and second electrical contacts.

6. The wearable device of claim 1, further comprising a wireless communication interface that transmit data indicative of the resistance of the skin between the first and second electrical contacts.

7. The wearable device of claim 1, wherein the capacitance sensor comprises a relaxation oscillator, wherein an operational frequency of the relaxation oscillator is related to the capacitance of the skin between the first and second electrical contacts.

8. The wearable device of claim 1, wherein the first and second electrical contacts have a characteristic size between 1 millimeter and 5 millimeters.

9. The wearable device of claim 1, wherein the first and second electrical contacts are separated by a distance of between 1 millimeter and 50 millimeters.

10. The wearable device of claim 1, wherein the first and second electrical contacts are spring-loaded.

11. The wearable device of claim 1, wherein the housing is water-proof.

12. The wearable device of claim 1, further comprising:
a temperature sensor, wherein the temperature sensor is thermally coupled to at least one of the first and second electrical contacts such that the temperature sensor can be operated to obtain a measurement related to a temperature of the skin at the external body surface when the wearable device is mounted to the external body surface.

13. The wearable device of claim 1, further comprising a DC blocking capacitor, wherein the capacitance sensor is electronically coupled to the first electrical contact via the DC blocking capacitor.

14. The wearable device of claim 1, further comprising a mount that can mound the housing to the external body surface such that the first and second electrical contacts contact skin at the external body surface.

15. The wearable device of claim 1, further comprising:
a processor;
a computer readable medium, wherein the computer readable medium stores program instruction that are executable by the processor to perform functions comprising:
operating the electronics to obtain a measurement relating to resistance; and
operating the electronics to obtain a measurement relating to capacitance.

16. The wearable device of claim 15, wherein the functions further comprise:
determining a resistance of skin between the first and second electrical contacts based on the measurement relating to resistance.

17. The wearable device of claim 15, wherein the functions further comprise:
determining a capacitance of skin between the first and second electrical contacts based on the measurement relating to capacitance.

18. The wearable device of claim 15, wherein the functions further comprise:
determining whether the wearable device is mounted to skin based on the measurement relating to resistance and/or the measurement relating to capacitance.

19. The wearable device of claim 15, wherein operating the electronics to obtain a measurement relating to resistance comprises:
operating, during a first period of time, the electronic switch such that the electronic switch is closed;
charging, during the first period of time, the capacitor using the resistance sensor;
operating, during a second period of time, the electronic switch such that the electronic switch is closed; and
obtaining, during the second period of time, the measurement relating to resistance using the resistance sensor.

20. The wearable device of claim 19, wherein operating the electronics to obtain a measurement relating to capacitance comprises:
operating, during a third period of time, the electronic switch such that the electronic switch is open; and
obtaining, during the third period of time, the measurement relating to capacitance using the capacitance sensor.

* * * * *